(12) United States Patent
Majumdar

(10) Patent No.: US 11,996,169 B2
(45) Date of Patent: May 28, 2024

(54) METHODS AND SYSTEMS FOR GRAPHICAL USER INTERFACES FOR BIOLOGICAL DATA

(71) Applicant: Life Technologies Corporation, Carlsbad, CA (US)

(72) Inventor: Nivedita Sumi Majumdar, San Bruno, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 17/808,880

(22) Filed: Jun. 24, 2022

(65) Prior Publication Data
US 2022/0328136 A1    Oct. 13, 2022

Related U.S. Application Data

(62) Division of application No. 16/304,795, filed as application No. PCT/US2017/034776 on May 26, 2017, now Pat. No. 11,410,751.

(Continued)

(51) Int. Cl.
*G16B 45/00* (2019.01)
*G06F 16/16* (2019.01)
(Continued)

(52) U.S. Cl.
CPC .......... *G16B 45/00* (2019.02); *G06F 16/168* (2019.01); *G06F 16/26* (2019.01); *G06T 11/206* (2013.01); *G16B 20/00* (2019.02); *G16B 40/00* (2019.02)

(58) Field of Classification Search
CPC .................................................. G16B 45/00
(Continued)

(56) References Cited

U.S. PATENT DOCUMENTS 3,369,962 A * 2/1968 Hochner ................. B32B 27/00
                                                                525/472
3,548,381 A * 12/1970 Dirks .................... G11B 15/005
(Continued)

FOREIGN PATENT DOCUMENTS

CA      2765190 A1 * 12/2009   ......... A61K 31/4402
JP    2009072206 A      4/2009
(Continued)

OTHER PUBLICATIONS

A. Arribas-Gil et al., "Shape outlier detection and visualization for functional data: the outliergram", Biostatistics, vol. 15, No. 4, Oct. 1, 2014 (Oct. 1, 2014), pp. 603-619, XP055400378, GB ISSN: 1465-4644, DOI: 10.1093/biostatistics/kxu006.
(Continued)

*Primary Examiner* — Reza Nabi
(74) *Attorney, Agent, or Firm* — François A. Pelaez

(57) ABSTRACT

In one exemplary embodiment, a method computer-implemented method of generating an outlier wheel data visualization for a graphical user interface (GUI) is provided. The method includes receiving emission data from a plurality of amplification reactions. The method further includes generating an outlier wheel data visualization using the emission data including a plurality of lines, where each line included in the outlier wheel data visualization represents emission data from an amplification reaction of the plurality of amplification reactions, and each line having a length and a visual indicator. The length of each line represents growth of intensity of fluorescence of the emission data and the visual indicator indicates the associated cycle number of the emission data. Further, each line is associated with an angular position so that the plurality of lines is configured in a circular shape. The method includes displaying the outlier wheel data visualization on a GUI.

4 Claims, 19 Drawing Sheets

Related U.S. Application Data

(60) Provisional application No. 62/342,731, filed on May 27, 2016.

(51) Int. Cl.
  *G06F 16/26* (2019.01)
  *G06T 11/20* (2006.01)
  *G16B 20/00* (2019.01)
  *G16B 40/00* (2019.01)

(58) Field of Classification Search
  USPC .......................................................... 702/20
  See application file for complete search history.

(56) References Cited

U.S. PATENT DOCUMENTS

| | | | | |
|---|---|---|---|---|
| 3,702,886 | A * | 11/1972 | Argauer et al. | C10G 11/05 |
| | | | | 423/326 |
| 3,790,471 | A * | 2/1974 | Argauer et al. | C10G 35/095 |
| | | | | 208/138 |
| 7,272,506 | B2 * | 9/2007 | Glanowski | G16B 20/20 |
| | | | | 435/6.17 |
| 2003/0104461 | A1 * | 6/2003 | Muehlbauer | G01N 33/5044 |
| | | | | 435/6.12 |
| 2003/0143554 | A1 * | 7/2003 | Berres | G16B 40/10 |
| | | | | 435/6.1 |
| 2004/0126782 | A1 * | 7/2004 | Holden | G16B 40/30 |
| | | | | 435/6.14 |
| 2007/0172855 | A1 * | 7/2007 | Bitner | C12Q 1/6806 |
| | | | | 536/25.4 |
| 2008/0154512 | A1 * | 6/2008 | Leong | C12Q 1/6851 |
| | | | | 435/6.16 |
| 2008/0178653 | A1 * | 7/2008 | Gunstream | G01N 21/274 |
| | | | | 73/1.02 |
| 2008/0182264 | A1 * | 7/2008 | Gunstream | C12Q 1/6851 |
| | | | | 703/11 |
| 2009/0037117 | A1 * | 2/2009 | Cheng | G16B 40/10 |
| | | | | 702/20 |
| 2009/0093430 | A1 * | 4/2009 | Lockstone | C12Q 1/6883 |
| | | | | 435/6.16 |
| 2010/0055208 | A1 * | 3/2010 | Gokce | A01N 65/00 |
| | | | | 424/725 |
| 2011/0252051 | A1 * | 10/2011 | Sikora | G16B 40/30 |
| | | | | 707/769 |
| 2011/0252353 | A1 * | 10/2011 | Janaway | G06F 3/0482 |
| | | | | 715/771 |
| 2011/0311973 | A1 * | 12/2011 | Rabin | C12Q 1/6883 |
| | | | | 435/6.12 |
| 2012/0194522 | A1 * | 8/2012 | Majumdar | G06T 11/206 |
| | | | | 345/440 |
| 2013/0304390 | A1 * | 11/2013 | Leong | G16B 20/00 |
| | | | | 702/19 |
| 2014/0236496 | A1 * | 8/2014 | Janaway | G16B 40/10 |
| | | | | 702/19 |
| 2014/0255914 | A1 * | 9/2014 | Gao | C12Q 1/701 |
| | | | | 435/5 |
| 2014/0372953 | A1 * | 12/2014 | Laurance | G06F 3/04817 |
| | | | | 715/835 |
| 2015/0057171 | A1 * | 2/2015 | Collins | C12Q 1/6883 |
| | | | | 506/9 |
| 2015/0225790 | A1 * | 8/2015 | Connolly | C12Q 1/6883 |
| | | | | 506/10 |
| 2015/0269756 | A1 * | 9/2015 | Leong | G16B 45/00 |
| | | | | 345/440 |
| 2015/0278437 | A1 * | 10/2015 | Majumdar | G16B 40/00 |
| | | | | 702/19 |
| 2015/0365052 | A1 * | 12/2015 | Barton | H03F 3/245 |
| | | | | 330/295 |
| 2016/0275149 | A1 * | 9/2016 | Majumdar | G16B 45/00 |
| 2016/0312274 | A1 * | 10/2016 | Majumdar | G06F 17/18 |
| 2016/0321398 | A1 * | 11/2016 | Majumdar | G06F 3/0482 |
| 2017/0002400 | A1 * | 1/2017 | Hutchison | C12Q 1/686 |
| 2017/0116369 | A1 * | 4/2017 | Chowdhury | G16B 5/00 |
| 2017/0177792 | A1 * | 6/2017 | Majumdar | G16B 50/20 |
| 2018/0144094 | A1 * | 5/2018 | Majumdar | G16B 40/10 |
| 2018/0225415 | A1 * | 8/2018 | Majumdar | G06F 3/0481 |
| 2018/0233784 | A1 * | 8/2018 | Zhamu | H01M 10/052 |
| 2018/0241031 | A1 * | 8/2018 | Pan | H01M 4/364 |
| 2018/0294475 | A1 * | 10/2018 | Zhamu | H01M 4/366 |
| 2019/0024073 | A1 * | 1/2019 | Ekker | C12N 15/62 |
| 2019/0051902 | A1 * | 2/2019 | Zhamu | H01M 10/056 |
| 2019/0353613 | A1 * | 11/2019 | King | G16B 45/00 |
| 2020/0160938 | A1 * | 5/2020 | Majumdar | G06F 16/168 |
| 2021/0005286 | A1 * | 1/2021 | De Craene | C12Q 1/6844 |
| 2021/0082541 | A1 * | 3/2021 | Chen | G01N 30/8675 |
| 2022/0347182 | A1 * | 11/2022 | Bhutani | A61P 19/02 |

FOREIGN PATENT DOCUMENTS

| | | |
|---|---|---|
| JP | 2015231387 A | 12/2015 |
| WO | WO-2009143572 A1 | 12/2009 |
| WO | WO-2009143573 A1 | 12/2009 |

OTHER PUBLICATIONS

Chenyue Hu et al., "Biowheel: interactive visualization and exploration of biomedical data", bioRxiv, Jan. 11, 2017 (Jan. 11, 2017).
EP20169657.2, Extended European Search Report, dated Jul. 24, 2020, 8 pages.
International Preliminary Report on Patentability for International Application No. PCT/US17/34776 dated Nov. 27, 2018, 11 pages.
International Search Report and Written Opinion for Application No. PCT/US17/34776, dated Nov. 27, 2017, 16 pages.
Steven M Hill et al: "Inferring causal molecular networks: empirical assessment through a community-based effort", Nature Methods. vol. 13. No. 4, Feb. 22, 2016 (Feb. 22, 2016). pages 310-318.

* cited by examiner

METHODS AND SYSTEMS FOR GRAPHICAL USER INTERFACES FOR BIOLOGICAL DATA

CROSS-REFERENCE TO RELATED APPLICATIONS

This application is a divisional of U.S. Pat. No. 16,304,795 filed Nov. 27, 2018, which is a 371 of International Application No. PCT/US2017/034776 filed May 26, 2017, which claims the benefit of U.S. Provisional Application No. 62/342,731 filed May 27, 2016, all disclosures are herein incorporated by reference in their entirety.

BACKGROUND

Conventional systems for analyzing biological data comprise some type of device or modality that is configured to obtain the biological data. This data can then often be collected and analyzed by some form of computer application or applications. Moreover, in such conventional systems, a different application is needed for each type of data, which requires the user to go back and forth between applications to look at different types of data making it challenging to cross-correlate different data types of a biological sample, for example.

It should be clear, therefore, that the ability to cross correlate data, perform quality assurance checks, detect patterns in the data, look at large amounts of data, provide streamlined workflows, etc., is limited in such conventional systems. A biological study typically involves gathering and comparing various sets of biological data. While such conventional systems and applications have made such studies far easier, the limitations noted above require the user to manually compare various types of biological data and the full potential or promise of such applications cannot fully be recognized due to such system limitations.

For example, a user may run various qPCR-based experiments to gather distinct types of biological data, such as genotyping data or gene expression data, about a gene of interest to the study. The user may also run sequencing experiments. If the user wants to compare data for a particular sample or target across these various types of data sets using conventional techniques, the user will often manually move between applications to find relevant data (e.g., the same sample and then manually analyze or compare these data sets). Thus, combining and corroborating, performing detailed analytics, discovering new biological links, and understanding emergent patterns is left mainly up to the researcher to accomplish with heavily manual workflows. Such a process involves extraneous manual effort, is prone to error, and is limiting in today's world of information deluge.

SUMMARY

In one exemplary embodiment, a computer-implemented method of generating an outlier wheel data visualization for a graphical user interface (GUI) is provided. The method includes receiving emission data from a plurality of amplification reactions. The method further includes generating an outlier wheel data visualization using the emission data, the outlier wheel data visualization including a plurality of lines, where each line included in the outlier wheel data visualization represents emission data from an amplification reaction of the plurality of amplification reactions and each line has a length and a visual indicator. The length of each line represents growth of intensity of fluorescence of the emission data and the visual indicator indicates the associated cycle number of the emission data. Further, each line is associated with an angular position so that the plurality of lines are configured in a circular shape or oval, or each of the lines is disposed along one radial line of a plurality of radial lines proceeding from a common point. The method includes displaying the outlier wheel data visualization on a GUI.

In another exemplary embodiment, a system for generating an outlier wheel data visualization for a graphical user interface (GUI) is provided. The system includes a memory and a processor. The processor is configured to receive emission data from a plurality of amplification reactions, generate an outlier wheel data visualization using the emission data including a plurality of lines, where each line included in the outlier wheel data visualization represents emission data from an amplification reaction of the plurality of amplification reactions. Each line has a length and a visual indicator. The length of each line represents growth of intensity of fluorescence of the emission data and the visual indicator indicates the associated cycle number of the emission data. Each line is associated with an angular position so that the plurality of lines are configured in a circular or oval shape. In some embodiments, each line of the plurality of lines is disposed along one radial line of a plurality of radial lines proceeding from a common point. For example, the plurality of lines may be configured to form an arch of a circular or oval shape. The processor is further configured to display the outlier wheel data visualization on a GUI.

In another exemplary embodiment, a computer-implemented method of normalizing genotyping data is provided. The method includes receiving a set of emission data, where the emission data includes intensity of a first dye and intensity of a second dye. The first dye indicates presence of a first target allele, and the second dye indicates presence of a second target allele. The method further includes generating a plot of the set of emission data by plotting the intensity of the first dye versus the intensity of the second dye and normalizing the emission data in the plot based on an angular scaling factor.

In another exemplary embodiment, a system for normalizing genotyping data is provided. The system includes a memory and processor. The processor is configured to receive a set of emission data, where the emission data includes intensity of a first dye and intensity of a second dye. The first dye indicates presence of a first target allele, and the second dye indicates presence of a second target allele. The processor is further configured to generate a plot of the set of emission data by plotting the intensity of the first dye versus the intensity of the second dye and normalize the emission data in the plot based on an angular scaling factor.

DETAILED DESCRIPTION

Figure 1:
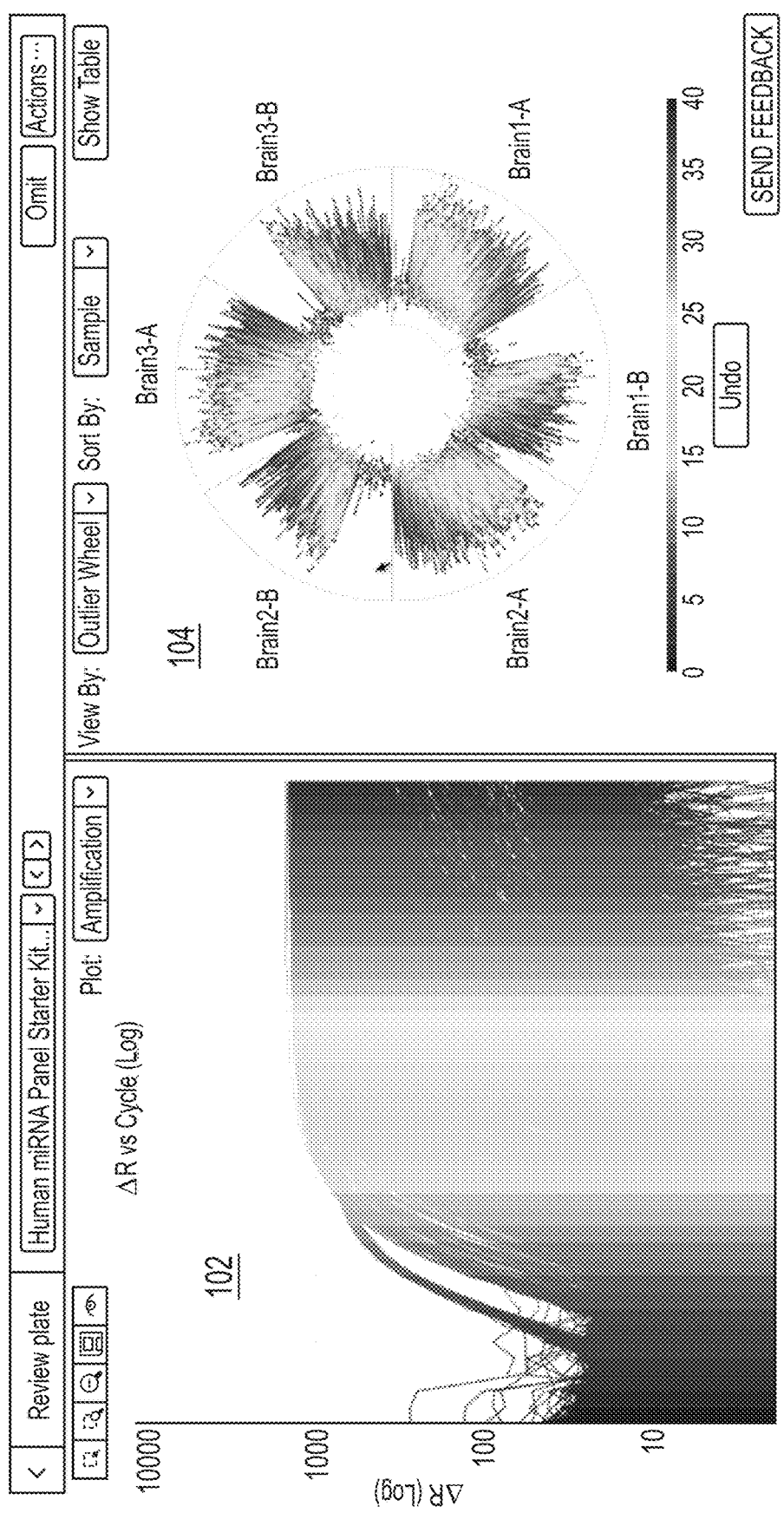
FIG. 1 illustrates an exemplary outlier wheel data visualization for a GUI according to various embodiments described herein.

To provide a more thorough understanding of various embodiments, the following description sets forth numerous specific details, such as specific configurations, parameters, examples, and the like. It should be recognized, however, that such description is not intended to limit the embodiments described to specific implementations, configurations, etc. Nor do the descriptions necessarily provide complete descriptions of the embodiments. As such, certain aspects, features, components, etc., may be omitted from the description of the various embodiments for ease of explanation.

In the systems and methods described herein, a user can obtain data from a plurality of devices or modalities, analyze the data, create a plurality of visualizations of the data, trigger various interactive functions for the data visualizations, cross correlate the data, launch various applications to view, analyze or manipulate the data all from within a single platform and interface. Examples of types of biological data that can be collected include, but are not limited to, technology vectors, biological molecule vectors, and the output data of various applications configured to work on these vectors. Examples of technological vectors can include, but are not limited to, CE sequencing, NGS sequencing, qPCR, dPCR, melt, microArrays, and combinations thereof. Examples of biological molecule vectors include, but are not limited to DNA, RNA, proteins, miRNA, etc. Examples of applications that produce output data based on these vectors include, but are not necessarily limited to genotyping applications, gene expression applications, absolute quantification applications, Copy Number Variation (CNV) analysis applications, Single Nucleotide Polymorphism (SNP) array analysis applications, High Resolution Melt (HRM) analysis applications, presence-absence analysis applications, etc. Thus, the outputs of these applications would also be biological data that can be used with the systems and methods described herein. Other information that can be consider biological data are meta-data, such as data that indicates disease information or treatment outcomes can also be used with the systems and methods described herein.

Quantitative polymerase chain reaction (qPCR) instruments or cyclers allow data to be collected during each cycle of the PCR process. PCR data can be collected at each cycle using an optical system within the qPCR instrument that can detect electromagnetic radiation emitted by one or more labeling probes attached to each nucleic acid sample analyzed by the qPCR instrument. In these examples, the PCR data, includes one or more labeling probe intensity values for each sample at each cycle or at each time associated with a cycle.

As one of ordinary skill in the art would understand, a PCR analysis is performed on a thermal cycling instrument, which has various protocols for progressing though a plurality of thermal cycles in order to amplify a target nucleic acid. In various embodiments of the present teachings, the number of cycles performed for the amplification may be between about 20-40 cycles. For various embodiments of the present teachings, the number of cycles performed for the amplification may be greater than 40 cycles. For amplification of a target nucleic acid a thermal cycling instrument may perform a first thermal cycle of a PCR experiment in a certain cycle time that may be associated with a first thermal cycle number.

Outlier Wheel Data Visualization

According to various embodiments described herein, an outlier wheel data visualization for a graphical user interface (GUI) may be used to present biological data in a way that can allow for more apparent identification of outlier amplification data. An outlier wheel also represents the biological data in a way that allows for efficient filtering and intuitive drill down to information that may not be as apparent in more traditional types of data visualizations.

FIG. 1 illustrates an exemplary GUI 100 including an outlier wheel data visualization 104 according to various embodiments described herein. FIG. 1 illustrates an amplification curve plot 102 of biological amplification data for a plurality of amplification reactions. The plurality of amplification reactions may include amplification data from a plurality of replicates of a biological sample and/or a plurality of replicates from a plurality of biological samples. Amplification curve plot 102 plots fluorescence data from each sample versus amplification cycle number. In amplification curve plot 102, the individual amplification curves may correspond to individual amplification reactions, such as reactions within a reaction confinement region (e.g., through-hole, well, microwell, or the like) of a PCR instrument. The number of amplification curves in amplification curve plot 102 makes it difficult to gather useful data from the amplification curve plot 102. With a large number of amplification reactions, data overplotting generates a crowded plot that creates problems with discerning trends or characteristics for individual amplification curves or a subset of amplification curves.

Alongside amplification curve plot 102 is an outlier wheel data visualization 104 according to various embodiments described herein. Outlier wheel data visualization 104 displays data from amplification curve plot 102 in a different way. Accordingly, different characteristics of the data may be more easily discernible. In addition, outlier wheel data visualization 104 comprises dynamic and interactive functionality such that the visualized data can be efficiently selected and filtered. In another embodiment, an interactive coordination between amplification curve plot 102 and outlier wheel data visualization 104 provides additional data views to enable trend or pattern detection by a user.

Figure 2:
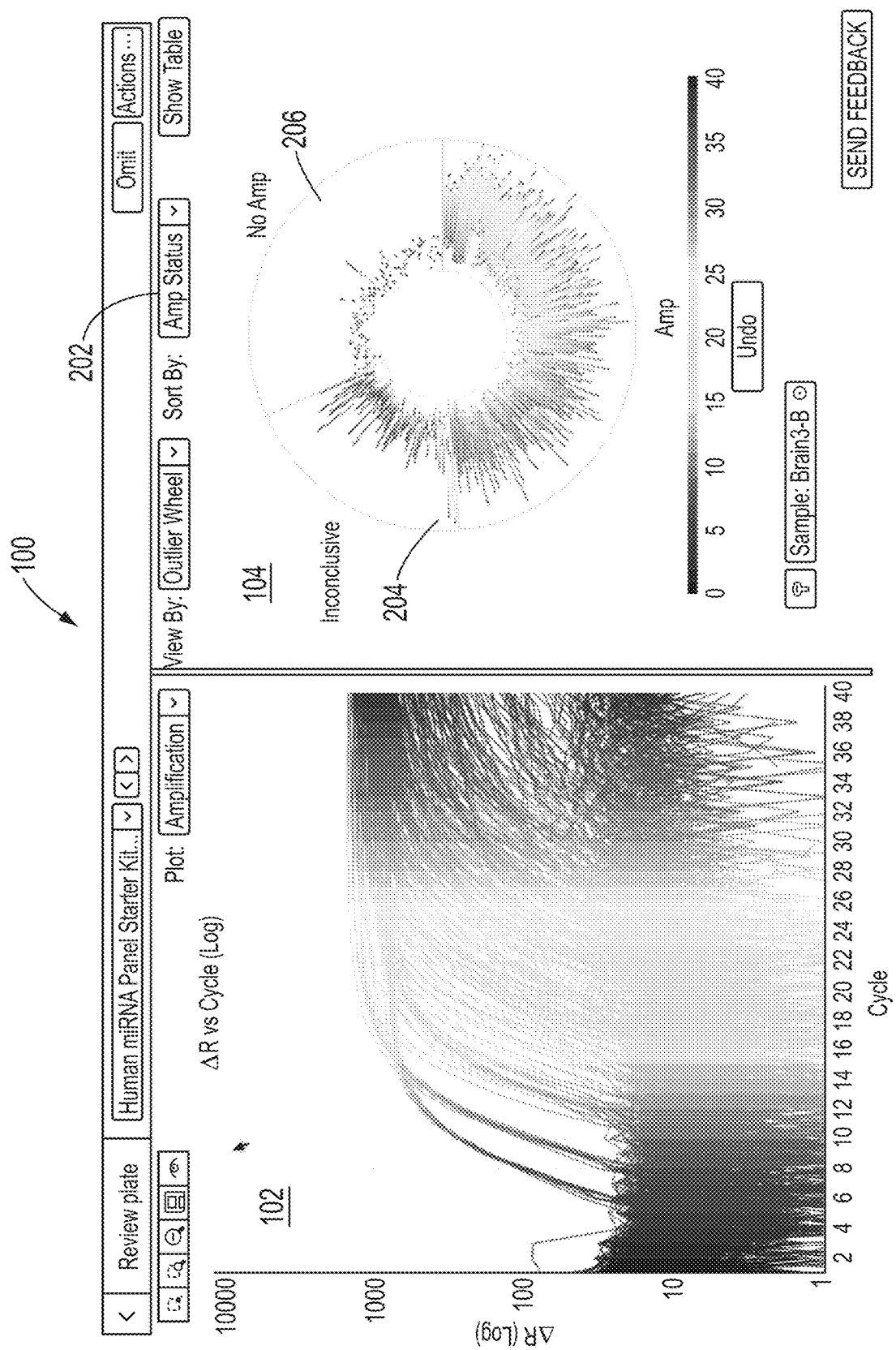
FIG. 2 illustrates data selection within an outlier wheel data visualization for a GUI according to various embodiments described herein.

FIG. 2 illustrates data selection within the outlier wheel data visualization 104 for a GUI 100 according to various embodiments described herein. A user may want to visualize the biological data by sample type and/or amplification status. Amplification status may be no amplification, amplification, or inconclusive, for example. The amplification status may have been previously determined by a processor. For example, PCR data (e.g., detected fluorescence over a predetermined number of PCR cycles) from the amplification reactions may have been analyzed by a processor such that a detection status algorithm processes the PCR data to determine the amplification status. In this embodiment, any suitable detection status algorithm may be implemented.

In this example, biological data from a biological sample is selected to be shown in the amplification curve plot 102 and outlier wheel data visualization 104. Upon selection of the biological sample to be shown, the amplification curve plot 102 and outlier wheel data visualization 104 are dynamically adjusted to show the amplification curves associated with the selected biological sample.

Figure 3:
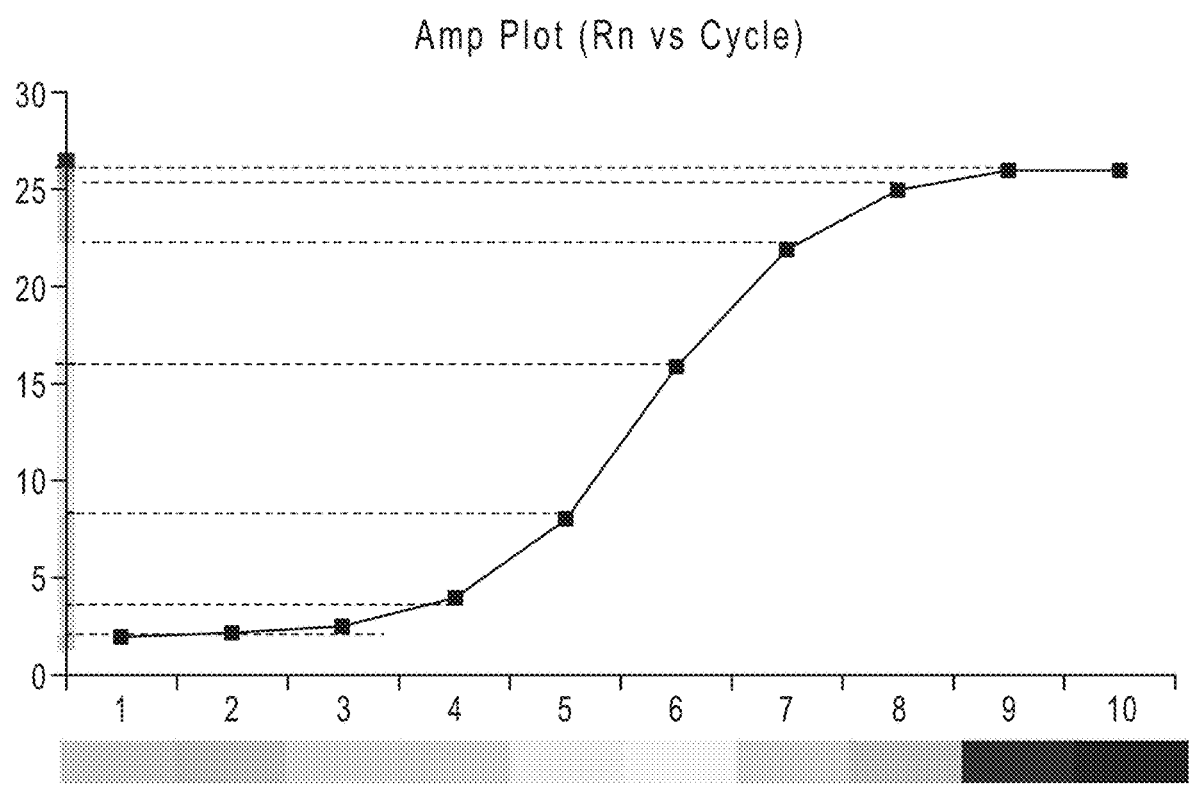
FIG. 3 illustrates how an amplification curve is transformed into an outlier wheel configuration according to various embodiments described herein.
Figure 3:
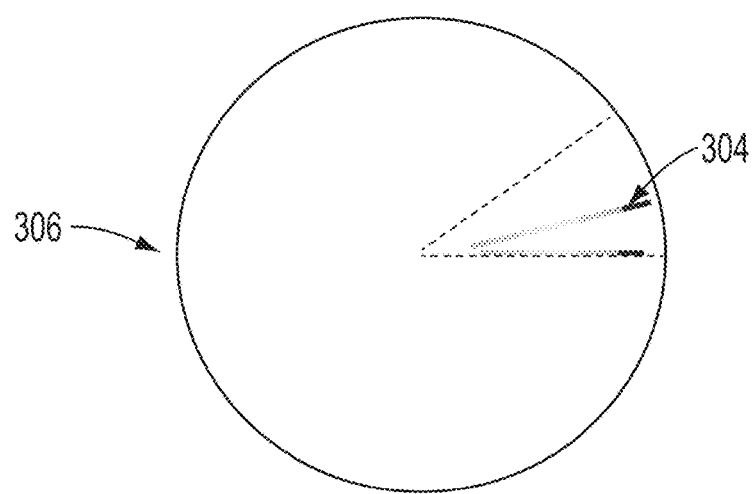

FIG. 3 illustrates how an amplification curve may be transformed into an outlier wheel configuration according to various embodiments described herein. In this illustrated embodiment, the outlier wheel data visualization is generated by projecting an amplification curve on a straight line and placed around the outlier wheel. Each amplification reaction (e.g., well, through-hole, or data point) can be assigned a unique angle ($\alpha$). For example, 360 degrees is divided by the total number of amplification curves to determine the step size in angle space for each amplification curve that gets plotted on the outlier wheel. In some embodiments, amplification reaction position (e.g., assigned angle) on the circle can be determined based on the attribute selected for sorting the wheel. In the example of FIG. 1, the outlier wheel is arranged by sample type.

The outlier wheel data visualization represents amplification curve data using a visual indicator, such as color, and length. In the illustrated embodiment, the visual indicator represents cycle number and the length represents the growth in fluorescence in that cycle. With reference back to FIG. 1, each amplification curve in amplification curve plot 102 corresponds to a line in the outlier wheel data visualization 104. At each angle in the circular format of the outlier wheel data visualization 104, one amplification curve is represented by a colored line of a certain length (e.g., proportional to a fluorescence signal). In FIG. 3, amplification curve 302 is shown in outlier wheel data visualization 306 as a single line 304. Line 304 represents the same data as in amplification curve 302. In the illustrated embodiment, the total length of the line represents the total growth in fluorescence across all amplification cycles. Each color of single line 304 corresponds to a particular amplification cycle and the length of each colored segment represents the growth in the corresponding amplification cycle. In other embodiments, other line characteristics such as line thickness and/or line style (e.g., solid, dashed, dotted, squiggled, etc.) can represent any other suitable variable, metric, or value of, for example, an amplification curve/amplification reaction. For example, any of color, length, thickness, and/or line style can represent amplification cycle, growth (e.g., during an amplification cycle), noise values, a second derivative of detected fluorescence, and any other suitable value or characteristic.

Although various embodiments and figures have been described using a circular shape in depicting the plurality of lines, those of ordinary skill in the art would appreciate based on the present disclosure and teachings, that the plurality of lines may be configured in any other suitable orientation or shape. For example, the plurality of lines (e.g., comprising segments of different colors) may be oriented along a line, which line may have a horizontal, vertical, or angled orientation. In such a configuration, the plurality of lines may be perpendicular to the configuration line and/or may be sorted into groups about the configuration line in a similar manner to the circular configuration illustrated herein. One of ordinary skill in the art would readily understand that the plurality of lines may be configured in other suitable shapes (e.g., square, rectangle, other polygons, and the like).

The user may also wish to sort the data by a certain characteristic. Referring back to FIG. 2, the user is able to select the type of characteristic to sort by in drop-down box 202. In the example shown in FIG. 2, the outlier wheel data configuration 104 displays the data by amplification status. In one portion of the outlier wheel 204, the amplification curves that were determined to be inconclusive are displayed. In another portion of the outlier wheel 206, the amplification curves that were determined to be not amplified are displayed.

Figure 5:
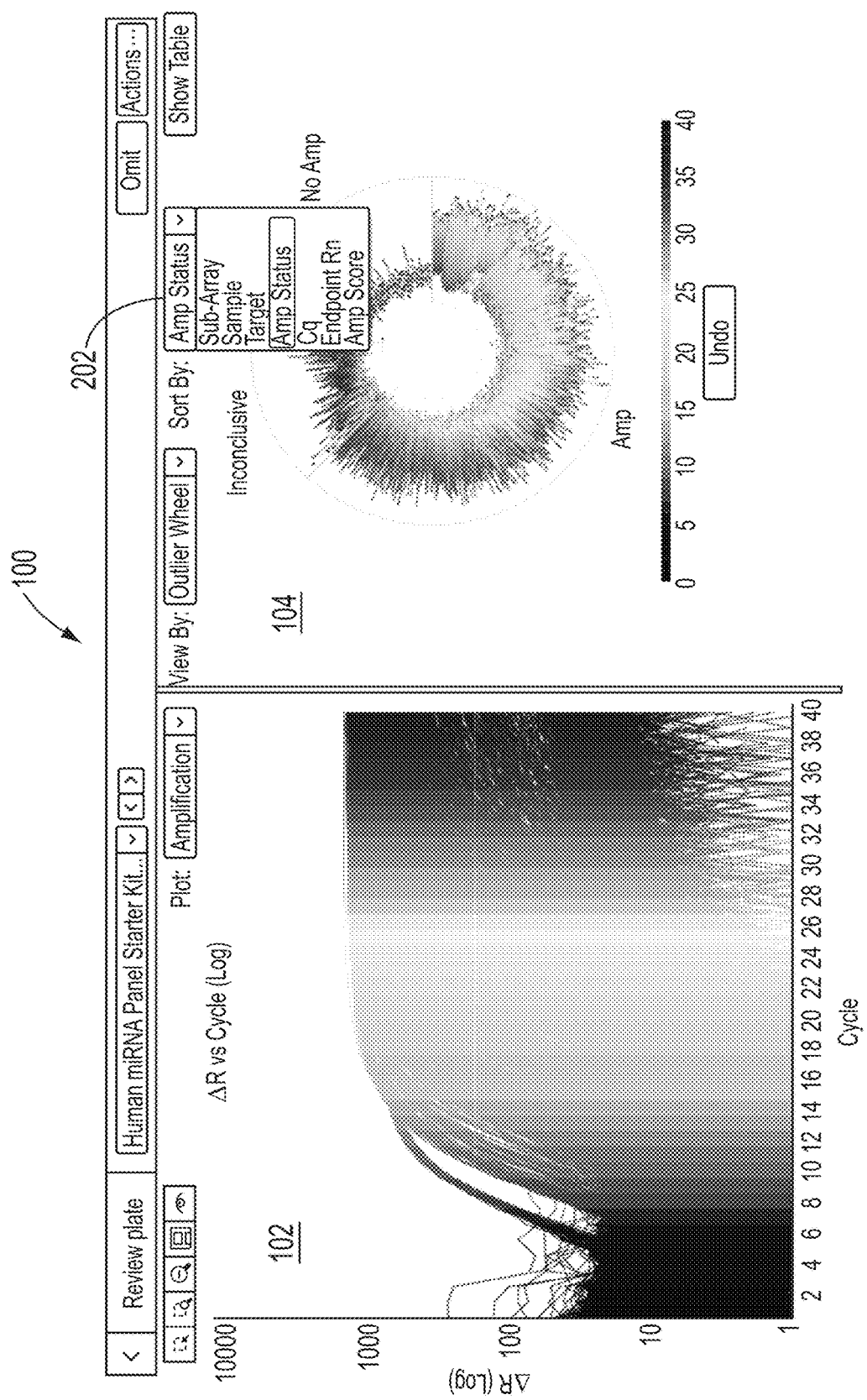
FIG. 5 illustrates different sortable data characteristics of the data in the outlier wheel according to various embodiments described herein.

Another example of displaying sorted data in the outlier wheel data configuration 104 is shown in FIG. 5. Drop down box 202 illustrate sorting options sub-array, sample, target, amplification status, quantification cycle (Cq), endpoint run, and amplification score. The outlier wheel data illustrated in FIG. 5 (which may be similar to that shown in FIG. 2) may be dynamically sorted according to the selected sorting options from drop down box 202. For example, the list in the drop-down menu in FIG. 5 may include a selection labeled "sub-array", the selection of which changes sorting of biological data about the wheel to be according to reaction chamber location (e.g., location within an amplification substrate, such as a through-hole plate or chip comprising wells). Similarly, the drop-down menu may include another selection labeled "quantification cycle", the selection of which changes sorting of amplification data about the wheel to be according to quantification cycle. The drop down menu may also include another selection labeled "target", the selections of which sorts biological data according to the particular target (e.g., target nucleic acid). FIGS. 1 and 7 illustrate outlier wheel data configuration 104 sorted by sample.

Figure 4:
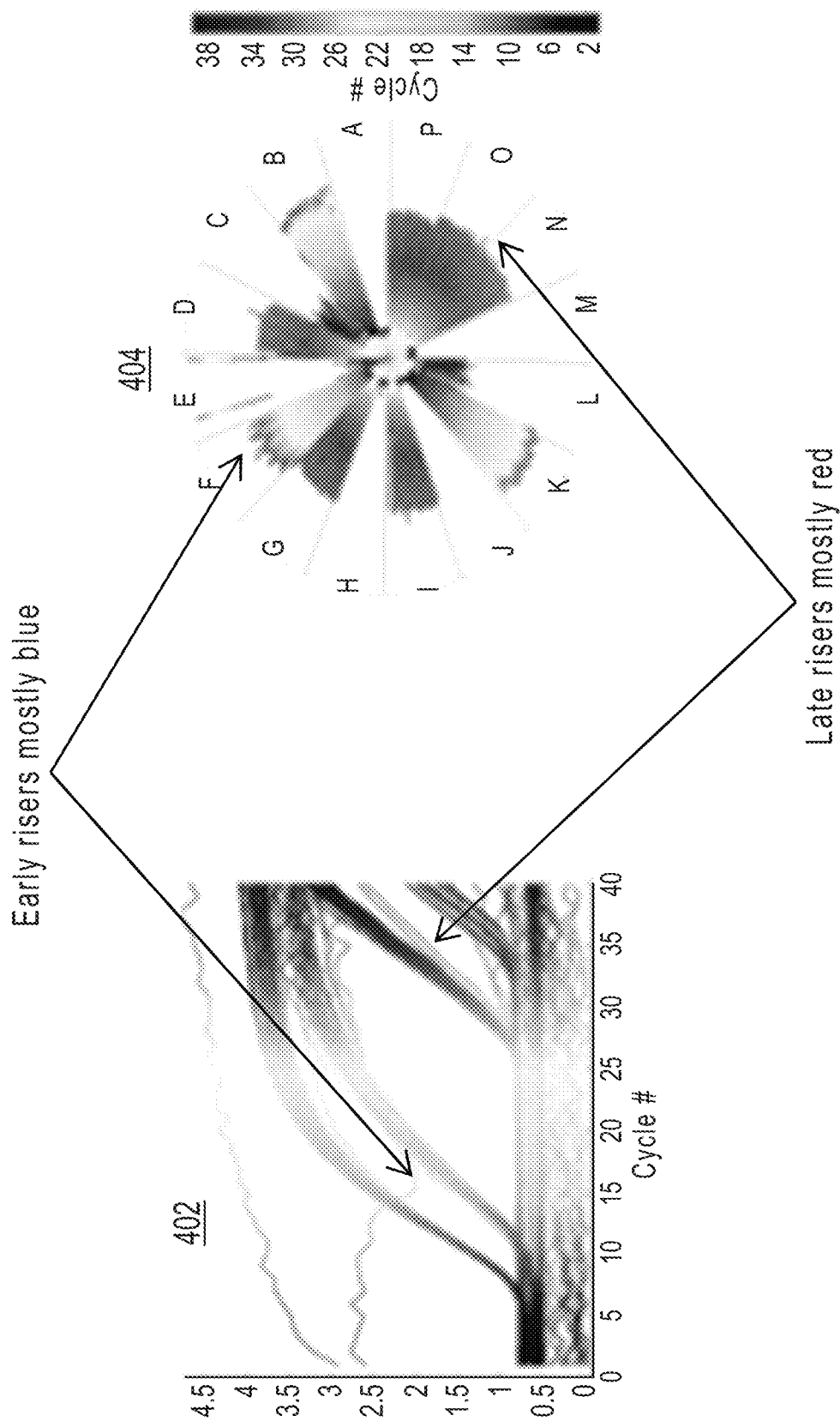
FIG. 4 illustrates visual indicators of an outlier wheel indicate amplification curve shape according to various embodiments described herein.

FIG. 4 illustrates visual indicators of an outlier wheel that each indicate amplification curve shape according to various embodiments described herein. The visual indicators of outlier wheel data visualization 404 indicate the shape of the amplification curve in amplification curve plot 402. For example, since a visual indicator such as color corresponds to the cycle number, the color in the outlier wheel data visualization 404 can indicate whether the reaction amplified in an early amplification cycle or a late amplification cycle.

Figure 6:
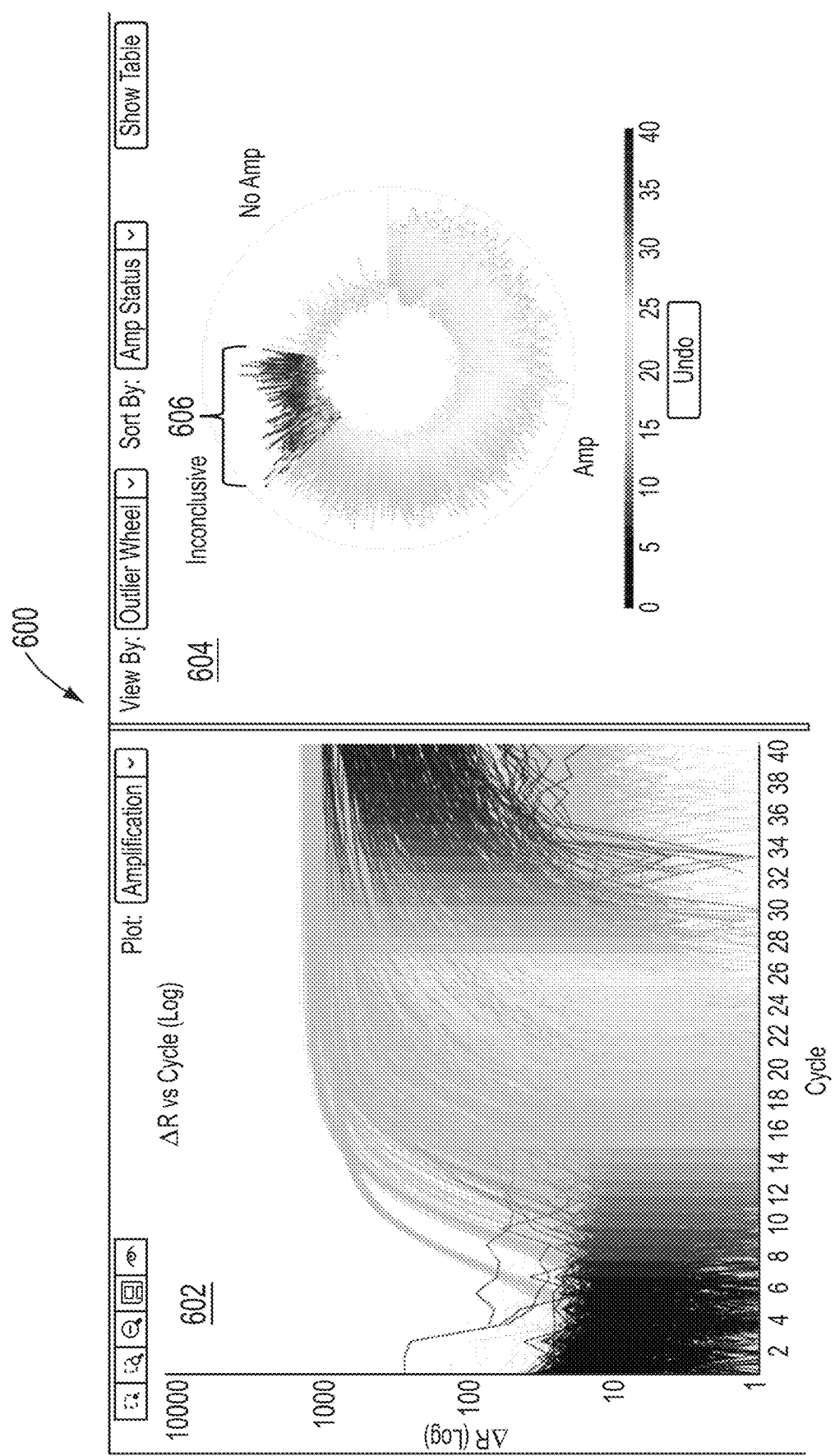
FIG. 6 illustrates synchronization of an amplification plot and corresponding outlier wheel data visualization according to various embodiments described herein.

FIG. 6 illustrates synchronization of an amplification curve plot 602 and corresponding outlier wheel data visualization 604 for a GUI 600 according to various embodiments described herein. In this example, a user selects a portion of biological data 606 in the outlier wheel data visualization 604. As the user selects the portion 606, the amplification curve plot 602 dynamically adjusts to highlight the amplification curves that correspond to the biological data from portion 606 in the outlier wheel data visualization 604. For example, the corresponding amplification curves may be displayed in color while the remaining amplification curves (that do not correspond to data from portion 606) are displayed in grey scale, with a reduced brightness, or a different shade or set of colors. In another example, the corresponding amplification curves may be displayed in the foreground for amplification curve plot 602 while the remaining amplification curves and pushed to the background. In another example, amplification curve plot 602 may be dynamically adjusted to only display amplification curves that correspond to biological data from portion 606.

Figure 7A:
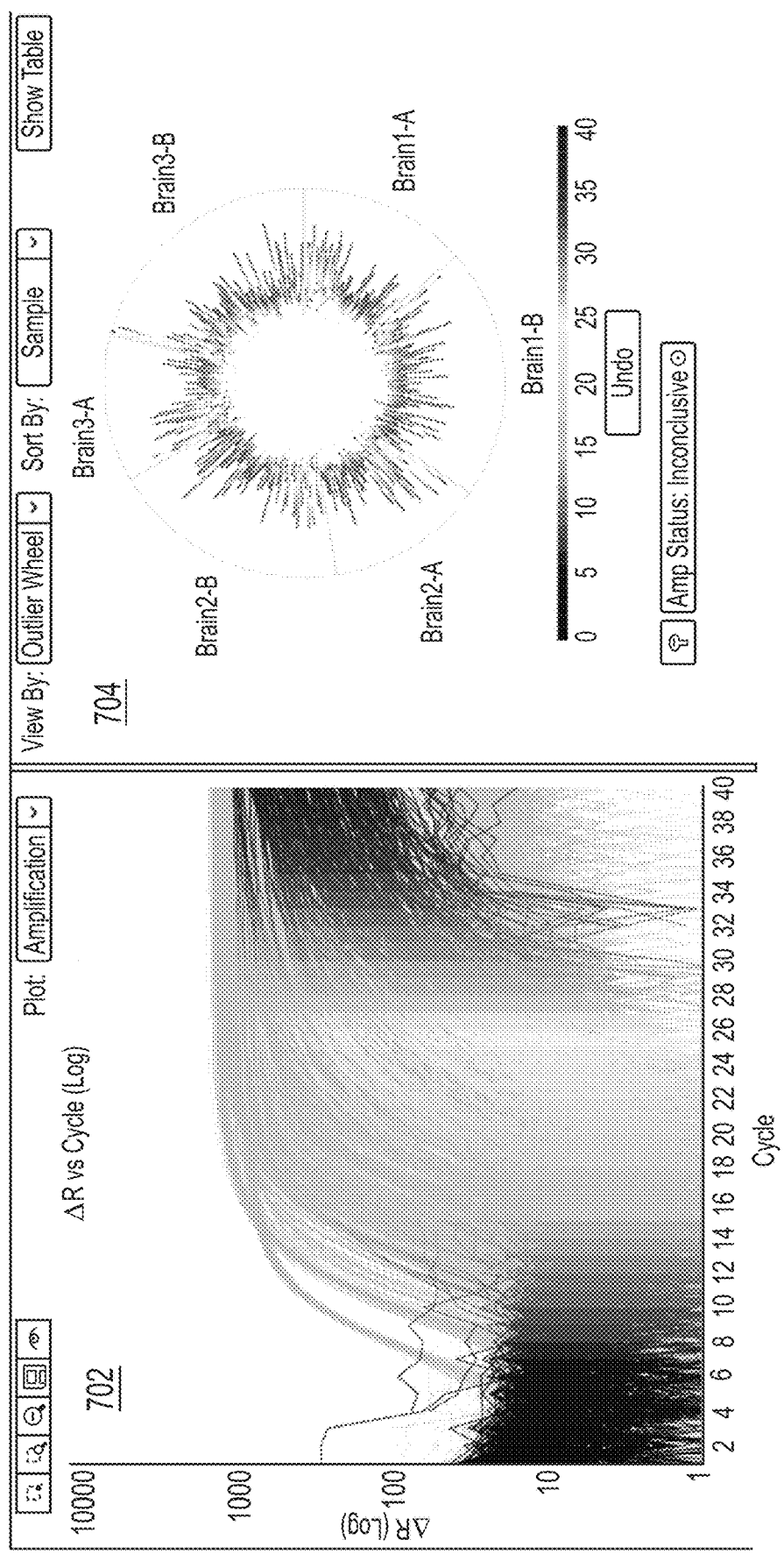
FIGS. 7A-7C illustrate dynamic changes of the outlier wheel based on data filtering according to various embodiments described herein.
Figure 7B:
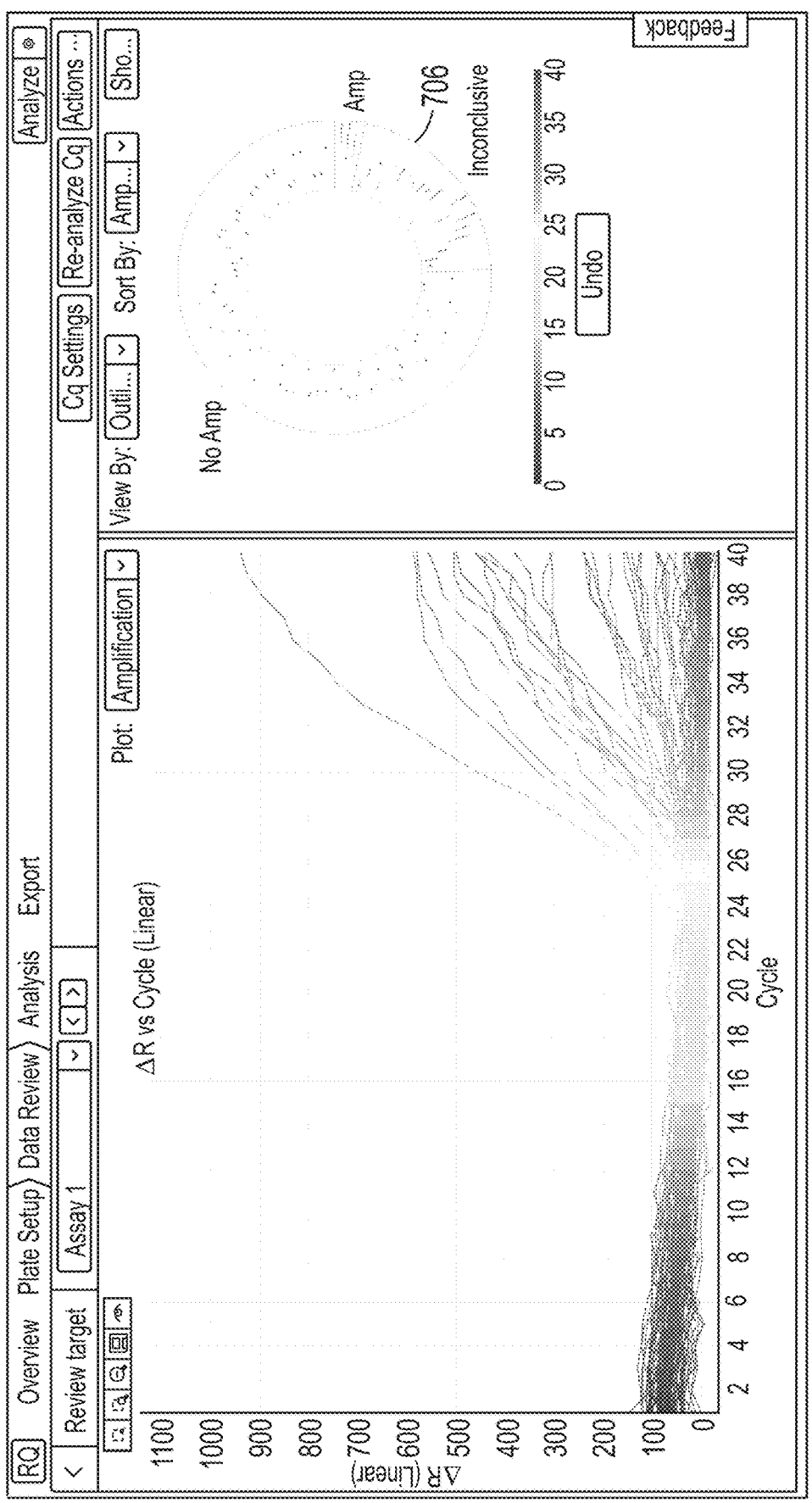
Figure 7C:
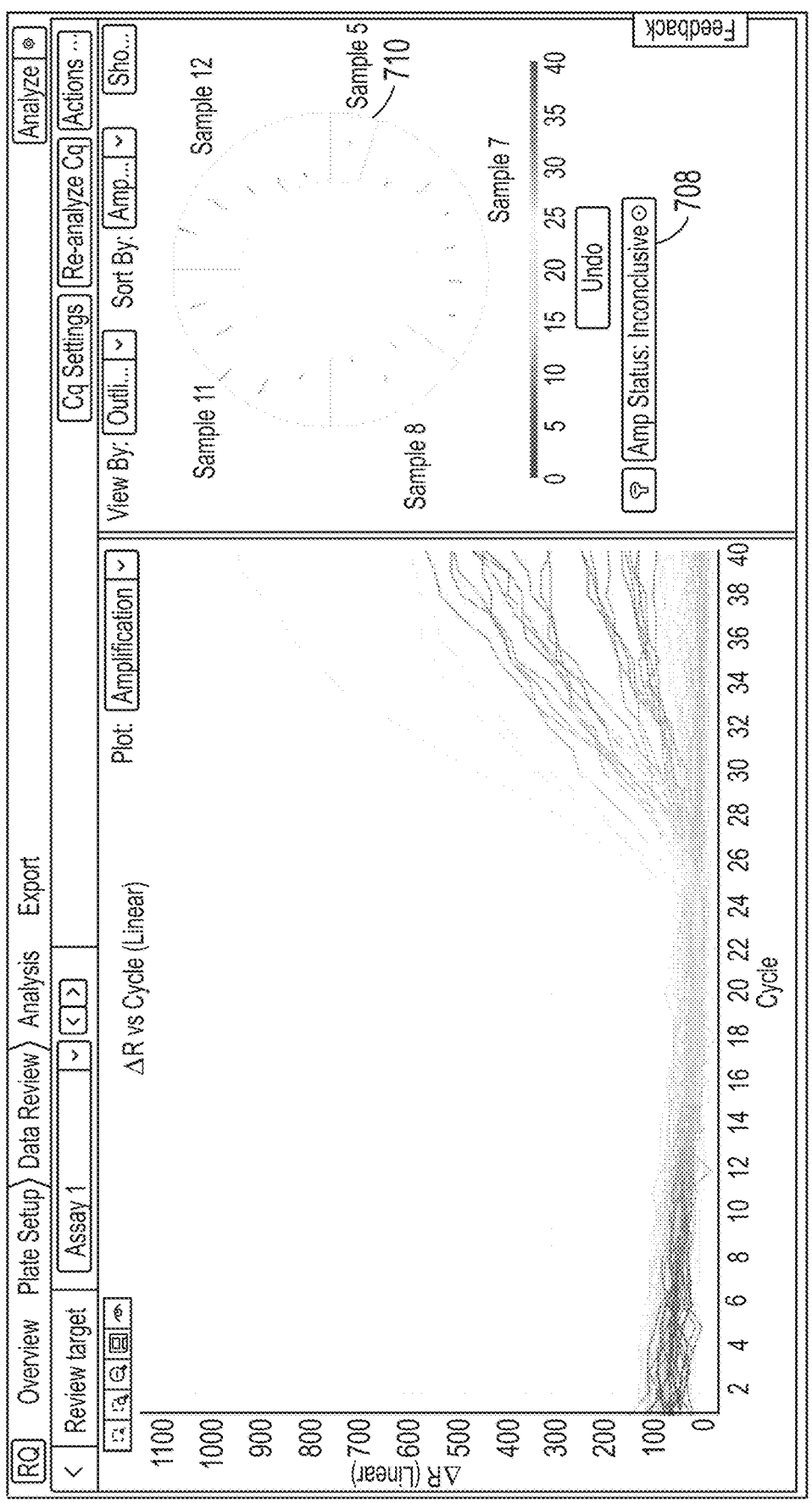

FIG. 7A-7C illustrate examples of dynamic and synchronous change of the outlier wheel data visualization 704 and amplification curve plot 702 based on data filtering according to various embodiments described herein. In some embodiments, outlier wheel data visualization 704 can correspond to outlier wheel data visualization 604 after applying a filter. For example, portion 606 of outlier wheel data visualization 604 may be selected such that the outlier wheel is filtered to show data from only portion 606. In this example, data from selected portion 606 is distributed about 360° of outlier wheel data visualization 704. Such a filtering selection may be made by selecting portion 606 as a characteristic filter, for instance by double clicking on this portion of the outlier wheel and/or dragging a cursor about the data to define an angular range to be selected. In this example, outlier wheel data visualization 704 is filtered by the status of amplification inconclusiveness, or the angular range selected (corresponding to the characteristics for portion 606). Once filtered, the biological data displayed in outlier wheel data visualization 704 can be sorted according to various data characteristics, as described with reference to FIG. 5 and drop-down box 202.

FIGS. 7B-7C illustrate another embodiment of filtering the outlier wheel data visualization. In FIG. 7B the biological data in outlier wheel data visualization 704 is sorted by amplification status. Portion 706 corresponds to biological data with an inconclusive amplification status. Portion 706 can be selected as the characteristic filter for outlier wheel data visualization 704. In FIG. 7C the biological data in outlier wheel data visualization 704 has been filtered according to portion 706, that is filtered for biological data with an inconclusive amplification status. Filter indicator 708 displays a status indication for the one or more filters applied to outlier wheel data visualization 704. After filtering, the outlier wheel data visualization 704 is sorted by sample, as illustrated in FIG. 7C.

Once a filter is applied, additional portions of the filter outlier wheel can be selected as a filter to further refine the displayed data. For example, portion 710 of outlier wheel data visualization 704 corresponds to biological data from sample 5. Portion 710 can be selected as a characteristic filter where outlier wheel data visualization 704 is then filtered both for biological data with an inconclusive amplification status and biological data from sample 5. In this example, an additional filter indicator that corresponds to the filter by sample is displayed proximate to filter indicator 708. After the two filters are applied to outlier wheel data visualization 704, the filtered data can be sorted according to various data characteristics (as described with reference to FIG. 5 and drop-down box 202) and further filters may be selected to continue to refine the data displayed in the outlier wheel.

Furthermore, it should be recognized that data selection and filtering is not only synchronous in the amplification plot 702 and outlier wheel data visualization 704, but may also dynamically change the data displayed in a standard well table identifying each sample and corresponding location within a well plate. In some embodiments, selecting a portion of biological data shown in the outlier wheel data visualization 704 will change the amplification curve plot 702 to display only the selected corresponding biological data, and further only display the selected corresponding data in the corresponding well table.

Cluster Normalization

In genotyping applications, amplification data from different allelic targets are plotted together to be able to discriminate between the different allelic targets. This type of plot is called an allelic discrimination plot. An allelic discrimination plot indicates which samples include only the first allele, only the second allele, both the first and second alleles, or none of the alleles. However, these genotyping cluster positions have been known to shift in the fluorescence space when samples from other substrates (e.g., microtiter plates, sample cards, sample plates, sample chips, or the like) are combined, leading to increased scatter in the resulting genotyping clusters. This may lead to problems in overlaying historical data which may, for example, limit the use of historical data.

According to various embodiments described herein, genotyping data is normalized to be able to improve the ability of the processor to compare different sets of genotyping data. Due to some physical process that does not impact the biology being analyzed, the genotyping data can experience some translation within an allelic discrimination plot. This physical process may include run to run variation, lot to lot variation (lot of consumables, reagents, and/or assay reagents), instrument to instrument variation, and other suitable variation. According to various embodiments, a reverse transform can correct for this effect.

Figure 8:
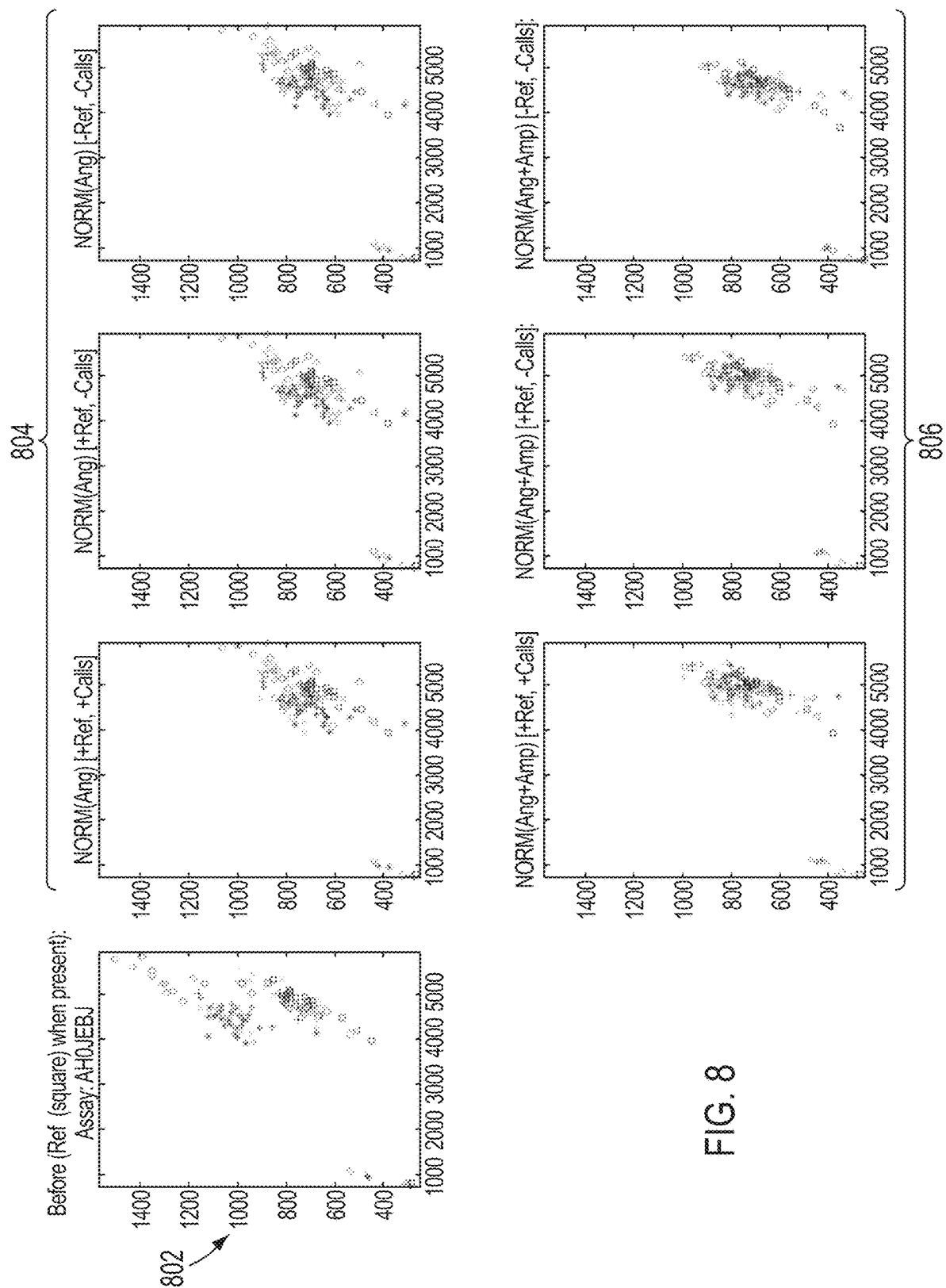
FIG. 8 illustrates an example of cluster normalization according to various embodiments described herein.

In one embodiment, cluster normalization includes choosing an anchor point between two genotyping data sets. For example, a first data set may be generated from a first substrate and a second data set may be generated from a second substrate. A single transformation can be applied to all points in the x-axis and y-axis on the first data set to line up the anchor points. According to one embodiment, the genotyping data may be normalized in the angles only. In another embodiment, the genotyping data may be normalized in the angles and the amplitudes. In yet another embodiment, the anchor may be rotated to the center of the most popular clusters between the target and reference substrates. In another embodiment, the most populated area is determined and the anchor is rotated to that point. In these examples, the rotation of a given data set's anchor to a determined point includes performing the same rotation to all data points in the x-axis and y-axis for the given data set FIG. 8 illustrates an example of cluster normalization according to various embodiments described herein. Plot 802 shows an original allelic discrimination plot including a plurality of data sets. Plots 804 show plot 802 normalized by angles according to various embodiments described herein. Plots 806 show plot 802 normalized by both angles and amplitudes according to various embodiments described herein.

Figure 9A:
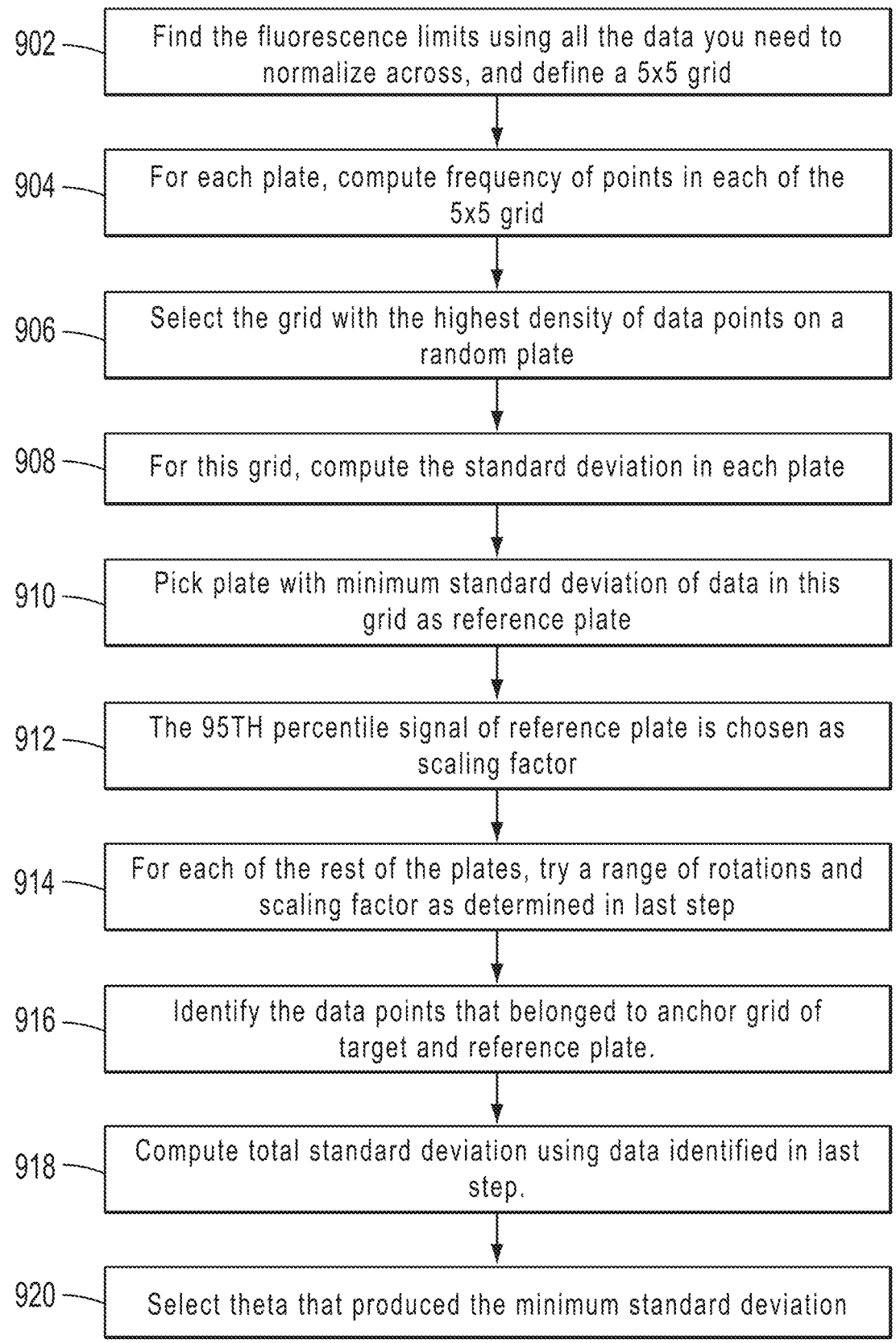
FIG. 9A illustrates an exemplary workflow of cluster normalization according to various embodiments described herein.

FIG. 9A illustrates an exemplary workflow of cluster normalization according to various embodiments described herein. The method begins in step 902 by finding the fluorescence limits using the data included in the plurality of data sets that are being compared. In some embodiments, the data sets may comprise amplification data from a plurality of substrates comprising a plurality of reaction chambers (e.g., plates or chips comprising wells, microwells, or through-holes). For example, the reaction chambers may contain reagents, such as one or more target nucleic acids and reagents for an amplification assay. When the plurality of substrates are subjected to thermal cycling, the reaction chambers emit fluorescence that indicates amplification of one or more target nucleic acids. In some embodiments, the reagents for the amplification assay can comprise a plurality of dyes, such as VIC™ and FAM®, where a first of the dyes indicates amplification of a first target and a second of the dyes indicates amplification of a second target.

In some embodiments, the set of received emission data from the plurality of substrates may include fluorescence data (intensity) of a first dye and fluorescence data (intensity) of a second dye. The first dye may indicate presence of a first target allele and the second dye may indicate presence of a second target allele. A plot of the set of emission data may be generated by plotting the intensity of the first dye versus the intensity of the second dye. FIG. 8 illustrates plots of fluorescence values using two dyes associated with two targets alleles generated from such emission data.

In an embodiment, a 5×5 grid may be generated based on the fluorescence values of the two dyes. For example, from the plurality of data sets, minimum and maximum fluorescence values (or intensity) of the first dye and minimum and maximum fluorescence values of the second dye may be determined. Those minimum and maximum value may be portioned into 5 bins, or groups, for each dye such that a 5×5 grid is formed. For example, the 5×5 grid can be superimposed on plot 802 based on the determined values for the 5 bins or groups for each of the plotted dyes. In other embodiments, an M×N grid may be implemented, where M and N may comprise any suitable values. For example, given a distribution of data points or a predicted distribution of data points (e.g., based on a number of targets or assay design), a density of data points or a predicted density of data points, and other attributes or predicted attributes for a plot, other suitable dimensions for a grid may improve the performed normalization.

In step 904, for each substrate, a frequency of points is computed in each grid of the 5×5 grid. For example, for each of the plurality of substrates (for fluorescence data detected from each of the plurality of substrates), a frequency of points may be computed within the individual grids of the 5×5 grid. In step 906, the grid from among the 5×5 grid with the highest density of data points on a random substrate is selected. For example, the grid from among the 5×5 grid with the highest number of data points generated from a random substrate may be selected. The selected grid may be referred to as the anchor grid. In step 908, the standard deviation for each substrate is computed for the selected grid. For example, for each of the plurality of substrates (for fluorescence data detected from each of the plurality of substrates), the standard deviation for the data points within the selected grid can be computed.

The substrate with the minimum standard deviation of data in the selected grid is selected as the reference substrate in step 910. The $95^{th}$ percentile signal of the reference substrate is chosen as the scaling factor in step 912. In some embodiments, a scaling factor may be implemented along with a rotation to normalize the data sets. The $95^{th}$ percentile signal (e.g., detected fluorescence level) can be used as the scaling factor when it is implemented. For each of the remaining substrates (other than the reference substrate), in step 914, a range of rotations is applied and, in some embodiments, the scaling factor, as determined in step 912, is applied. For example, a program may iterate over transformations to the data from a target substrate in the selected grid based on a range of rotation angles (θ), the iterations comprising a stepwise change in rotation angle for each transformation. In step 916, the data points that belong to the anchor grid of the target substrate and reference substrate are identified. The total standard deviation is computed in step 918 using data identified in step 916. For example, for each iteration that uses a stepwise change in rotation angle, the standard deviation for the identified data points may be computed. Finally, in step 920, the rotation angle (θ) that produced the minimum standard deviation is selected.

In some embodiments, a predetermined anchor point may be used as the reference point for data transformation rather than a selected anchor grid. For example, based on a plurality of inputs, such as the assay used for amplification, the instrumentation, the reagents, the dyes, and any other suitable input, an anchor point for data transformations may be predetermined. In some embodiments, a predicted range of fluorescence values may be used to determine the predetermined anchor point. In this example, the predetermined anchor point may be independent of the generated data sets, and thus may reduce variations in selected transformations across multiple experiments.

In some embodiments, the resultant transformation of the data points can be represented by the equations: X_normalized=TM×X_original; and Y_normalized=TM×Y_original. The transformation (TM), may be represented by equation TM=Signal scaling factor×[(cos(θ)−sin(θ)); (sin(θ)cos(θ)]. In embodiments where scaling is implemented, the factor may be represented by the equation Signal Scaling Factor=Upper 95th percentile of Signal Strength Reference Substrate/Upper 95th percentile of Signal Strength Target Substrate.

Figure 9B:
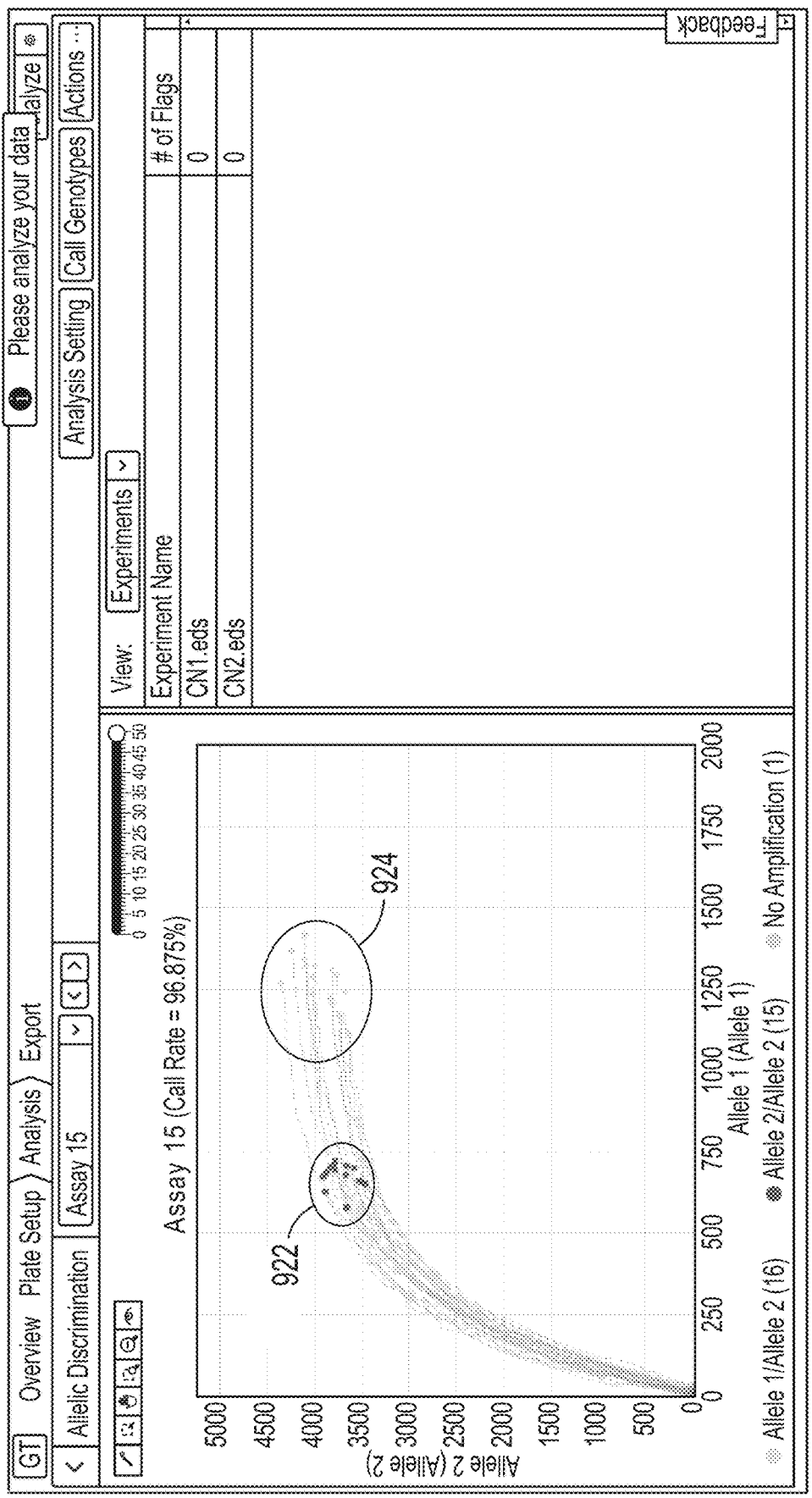
FIGS. 9B-9C illustrate another example of cluster normalization according to various embodiments described herein.
Figure 9C:
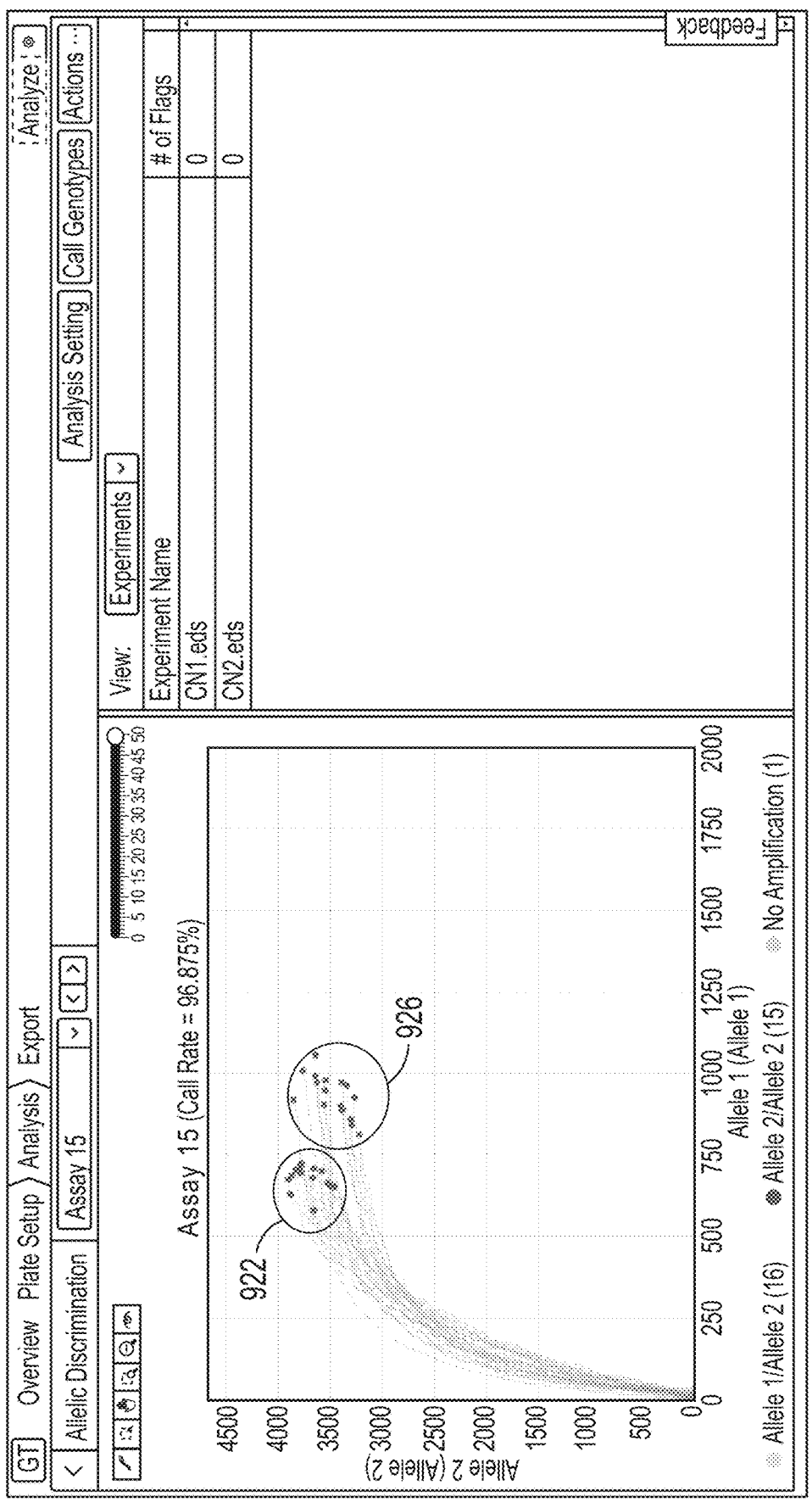

FIGS. 9B-9C illustrates an example of cluster normalization that correspond to the exemplary workflow described in FIG. 9A. In the illustrated example, fluoresce data for two dyes from two substrates is generated, and corresponding clusters 922 and 924 are displayed. Prior to normalization, the clusters are labeled as different alleles due to the disparity in the detected amplification data, as illustrated in FIG. 9B. After normalization using the described workflow from FIG. 9A, data from cluster 924 is transformed (e.g., using a selected rotation and scaling factor) and results in data cluster 926. As illustrated in FIG. 9B, after normalization cluster 922 and 926 are labeled as the same allele.

Figure 10:
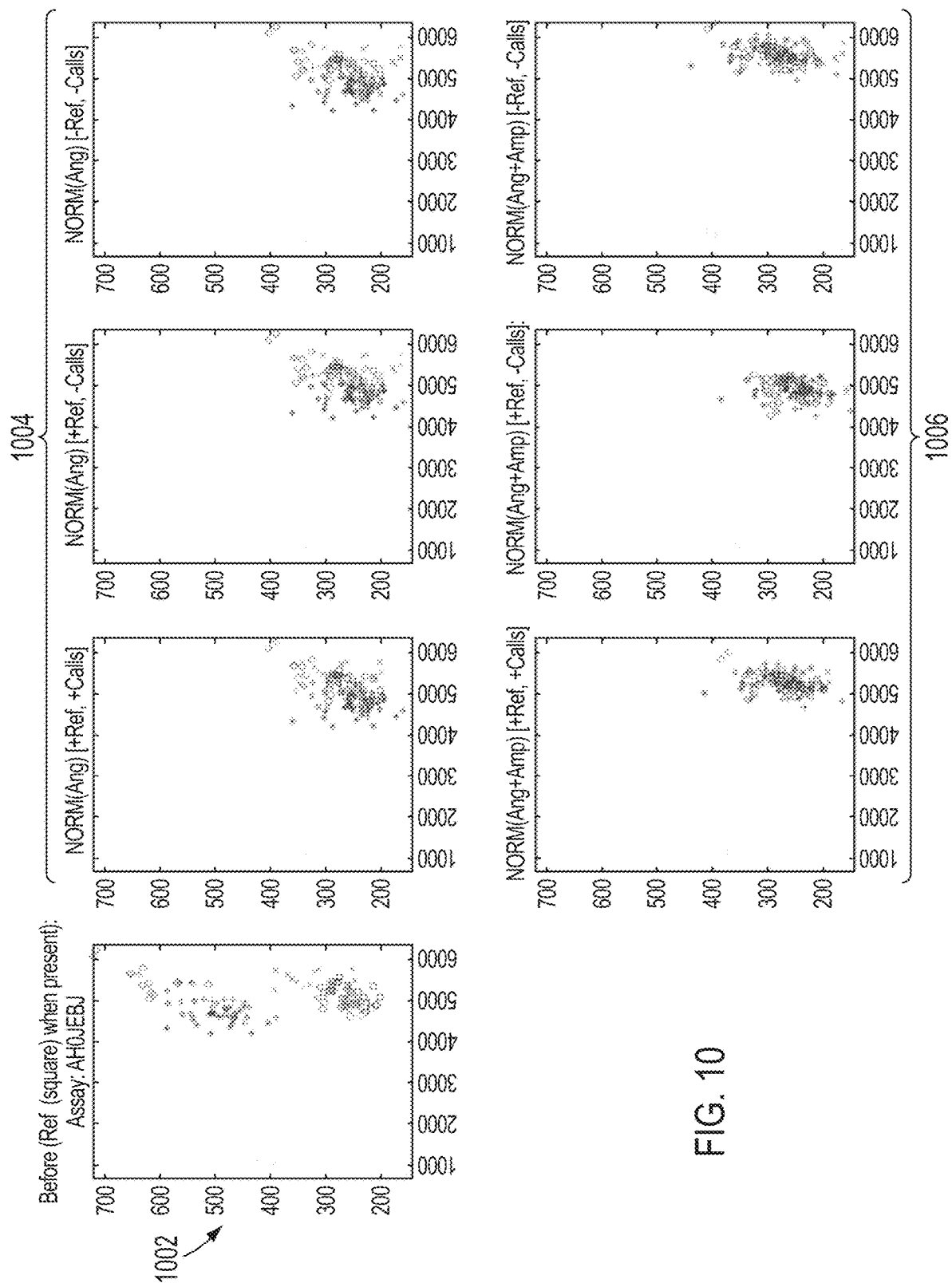
FIG. 10 illustrates another example of cluster normalization according to various embodiments described herein.
Figure 11:
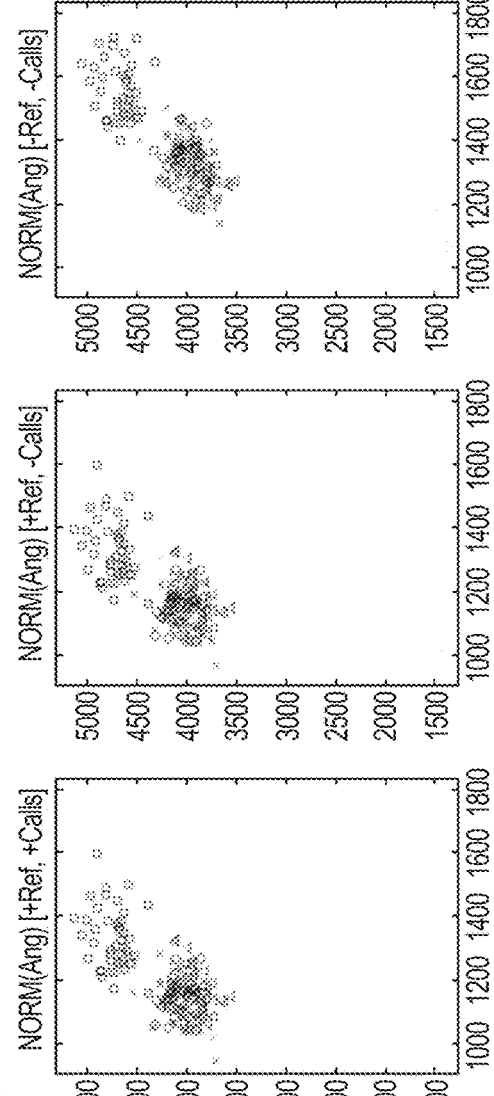
FIG. 11 illustrates yet another example of cluster normalization according to various embodiments described herein.
Figure 11:
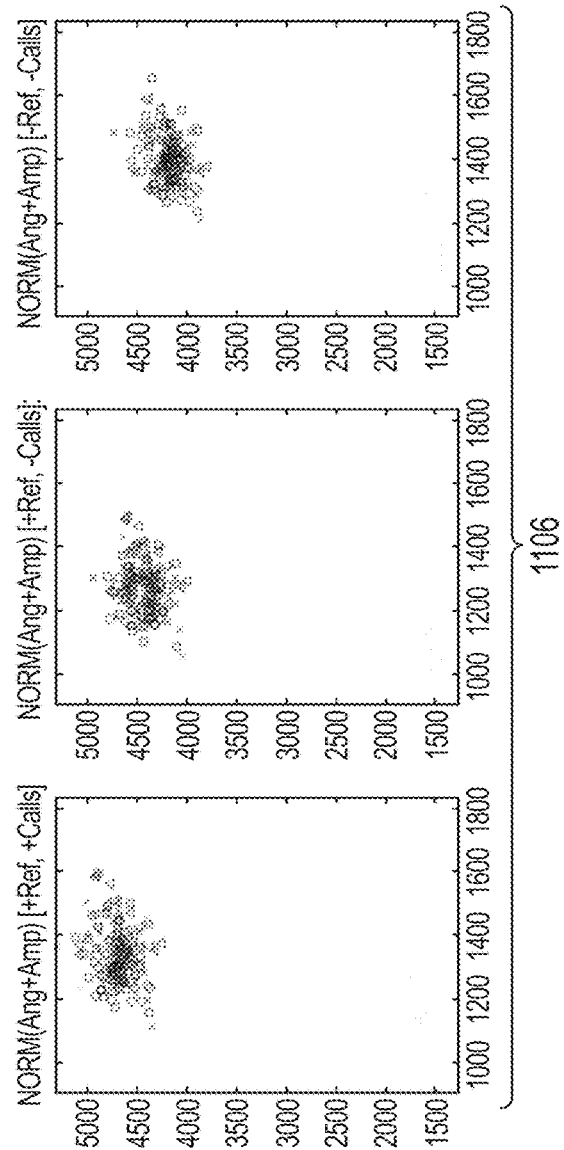
Figure 12:
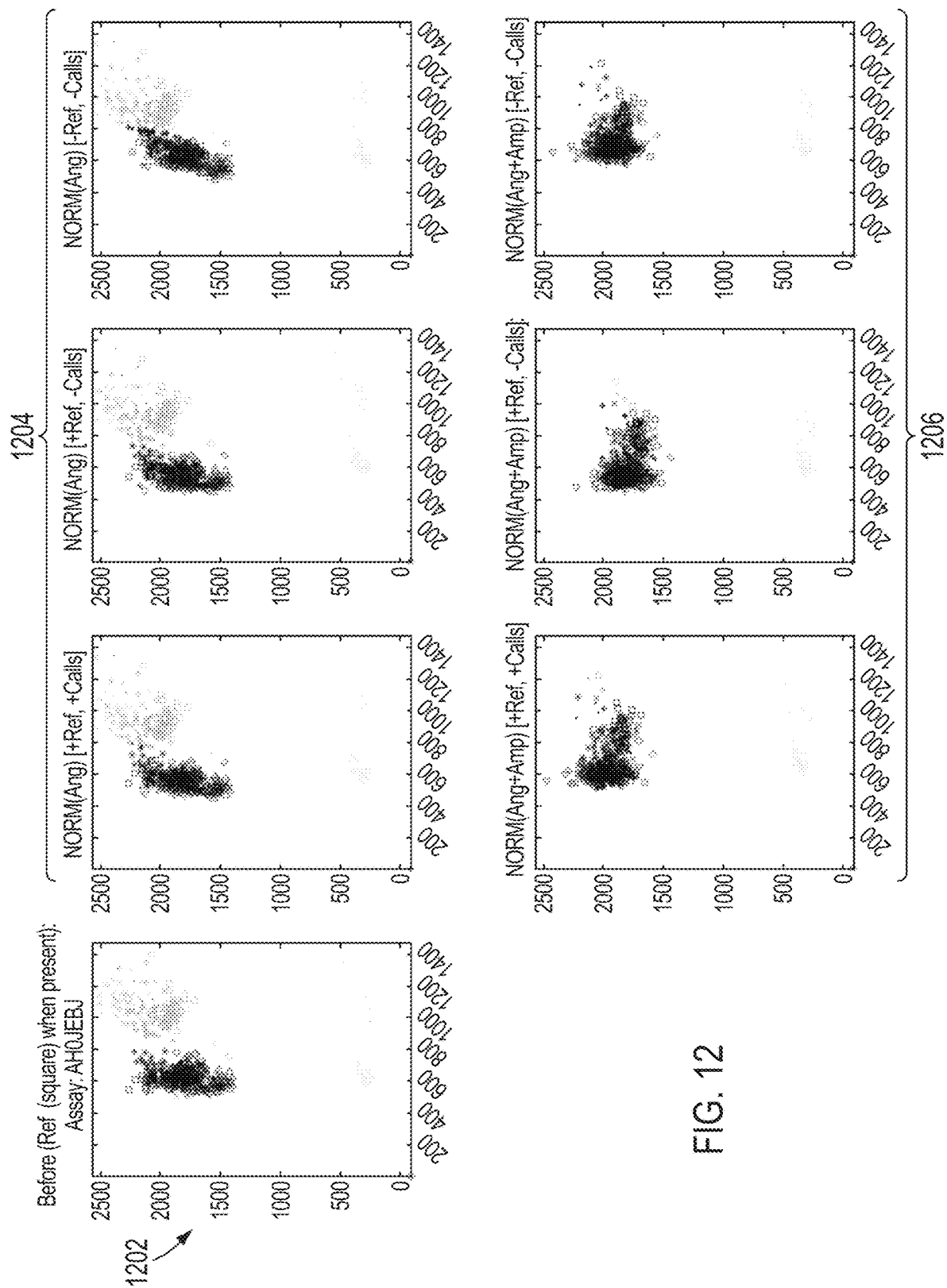
FIG. 12 illustrates yet another example of cluster normalization according to various embodiments described herein.

FIGS. 10, 11, and 12 illustrate additional examples of cluster normalization according to various embodiments described herein. With reference to FIG. 10, plot 1002 shows an original allelic discrimination plot including a plurality of data sets. Plots 1004 show plot 1002 normalized by angles according to various embodiments described herein. Plots 1006 show plot 1002 normalized by both angles and amplitudes (scaling factor) according to various embodiments described herein.

The leftmost plot from among plots 1004 illustrates normalization that transforms the data using a selected angle (e.g., no scaling) and that implements a user selected reference substrate and data calls when performing the normalization. For instance, rather than selecting a substrate based on standard deviation (as described in FIG. 9A) the normalization may be based on a user selected reference substrate. In addition, rather than determining an anchor grid (as described in FIG. 9A), automated data calls may be implemented when determining an anchor point for transformations. For example, a cluster may be identified based on automated data calls, and the center of the identified cluster may be used as the anchor point for transformations. The middle plot from among plots 1004 illustrates normalization that transforms the data using a selected angle (e.g., no scaling) and that implements a user selected reference, however, does not implement data calls. The rightmost plot from among plots 1004 illustrates normalization that transforms the data using a selected angle (e.g., no scaling) and that implements a reference substrate selected based on standard deviation and does not implement data calls.

The leftmost plot from among plots 1006 illustrates normalization that transforms the data using a selected angle and scaling, and that implements a user selected reference substrate and data calls when performing the normalization. The middle plot from among plots 1006 illustrates normalization that transforms the data using a selected angle and scaling, and that implements a user selected reference, however, does not implement data calls. The rightmost plot from among plots 1006 illustrates normalization that transforms the data using a selected angle and scaling, and that implements a reference substrate selected based on standard deviation and does not implement data calls.

With reference to FIG. 11, plot 1102 shows an original allelic discrimination plot including a plurality of data sets. Plots 1104 show plot 1102 normalized by angles according to various embodiments described herein. Plots 1106 show plot 1102 normalized by both angles and amplitudes (scaling factor) according to various embodiments described herein. The normalization techniques implemented for the leftmost, middle, and rightmost plots from among plots 1104 and 1106 correspond to the normalization techniques described with reference to the leftmost, middle, and rightmost plots from among plots 1004 and 1006.

With reference to FIG. 12, plot 1202 shows an original allelic discrimination plot including a plurality of data sets. Plots 1204 show plot 1202 normalized by angles according to various embodiments described herein. Plots 1206 show plot 1202 normalized by both angles and amplitudes according to various embodiments described herein. The normalization techniques implemented for the leftmost, middle, and rightmost plots from among plots 1204 and 1206 correspond to the normalization techniques described with reference to the leftmost, middle, and rightmost plots from among plots 1004 and 1006.

To evaluate the improvement of cluster normalized allelic discrimination plots over original cluster normalized allelic discrimination plots, the standard deviation, call rate, and accuracy of calls are compared.

A standard deviation of a cluster is determined by:

$$\sqrt{\frac{1}{n}\sum_{i=1}^{n}\|z_i - c\|}$$

$$\|z_i - c\| = (x_i - c_x)^2 + (y_i - c_y)^2$$

$$c = (c_x, c_y)$$

In the above equation, x and y correspond to fluorescence values for different fluorescence labeled data (e.g., VIC™ and FAM® dye values), c corresponds to the center of the grid for which the standard deviation is being computed, and n corresponds to the number of data points within the grid.

The call rate [UND=Conf.<95%] is determined by:

$$= (\#HETS + \#HOMO2 + \#HOMO1)/\# \text{ TOTAL}$$

For example, the call rate may be calculated based on sum of the heterozygous data calls, homozygous data calls of a first type, and homozygous data calls of a second type, where the sum is divided by the total number of data points (including other calls such as no amplification, invalid, and undetermined calls). Accuracy is related to the call agreement based on per substrate calls.

Figure 13:
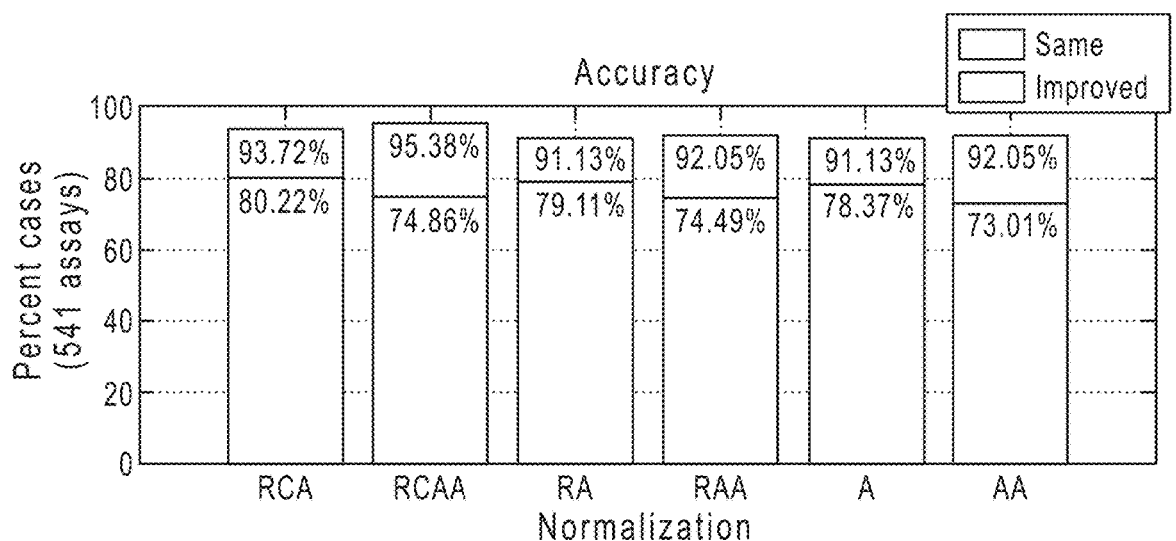
FIG. 13 illustrates the improvement of accuracy using the cluster normalization method according to various embodiment described herein.

FIG. 13 shows the percentage of data sets that showed improved accuracy, where RCA: +User Selected Reference Substrate+Automated Data Calls (Angles Only)

RCAA: +User Selected Reference Substrate+Automated Data Calls (Angles & Amplitudes or Scaling Factor)

RA: +User Selected Reference Substrate (Angles Only), No Automated Data Calls

Figure 14:
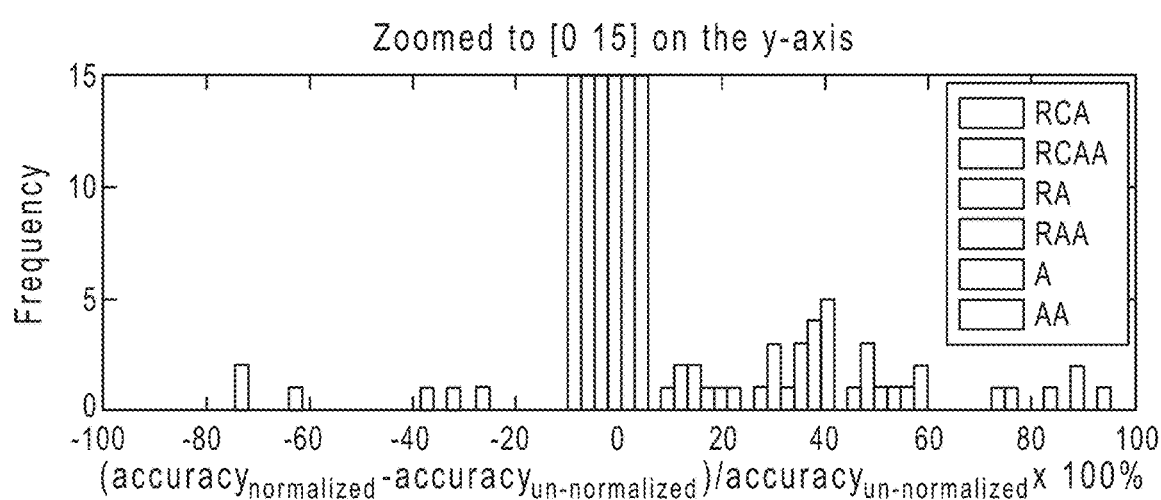
FIG. 14 illustrates the improvement of accuracy using the cluster normalization method according to various embodiment described herein.

RAA: +User Selected Reference Substrate (Angles & Amplitudes or Scaling Factor), No Automated Data Calls A: (Angles Only), No User Selected Reference Substrate, No Automated Data Calls AA: (Angles & Amplitudes or Scaling Factor), No User Selected Reference Substrate, No Automated Data Calls The assessment of accuracy in this example is based upon the automated calls obtained from single substrate for an assay. The assumption is that without the noise from overlaying many data sets, there is sufficient separation in the clusters to make accurate calls. The length of bars labeled "same" show the number of cases where the agreement between the normalized multi-substrate calls and the single substrates calls was the same as the agreement between the un-normalized multi-substrate calls and the single substrate calls, for each of the different normalization schemes. In other words, the "same" bars show cases where the call accuracy was not improved but did not become worse due to the normalization. The "improved" bars show the number of cases the agreement between the normalized multi-substrate calls and the single substrate calls were better than the un-normalized multi-substrate calls and the single substrate calls. FIG. 14 illustrates the number of cases where the amplification status calls improved, remained the same, or became worse, binned by the percent change in the call accuracy.

Figure 15:
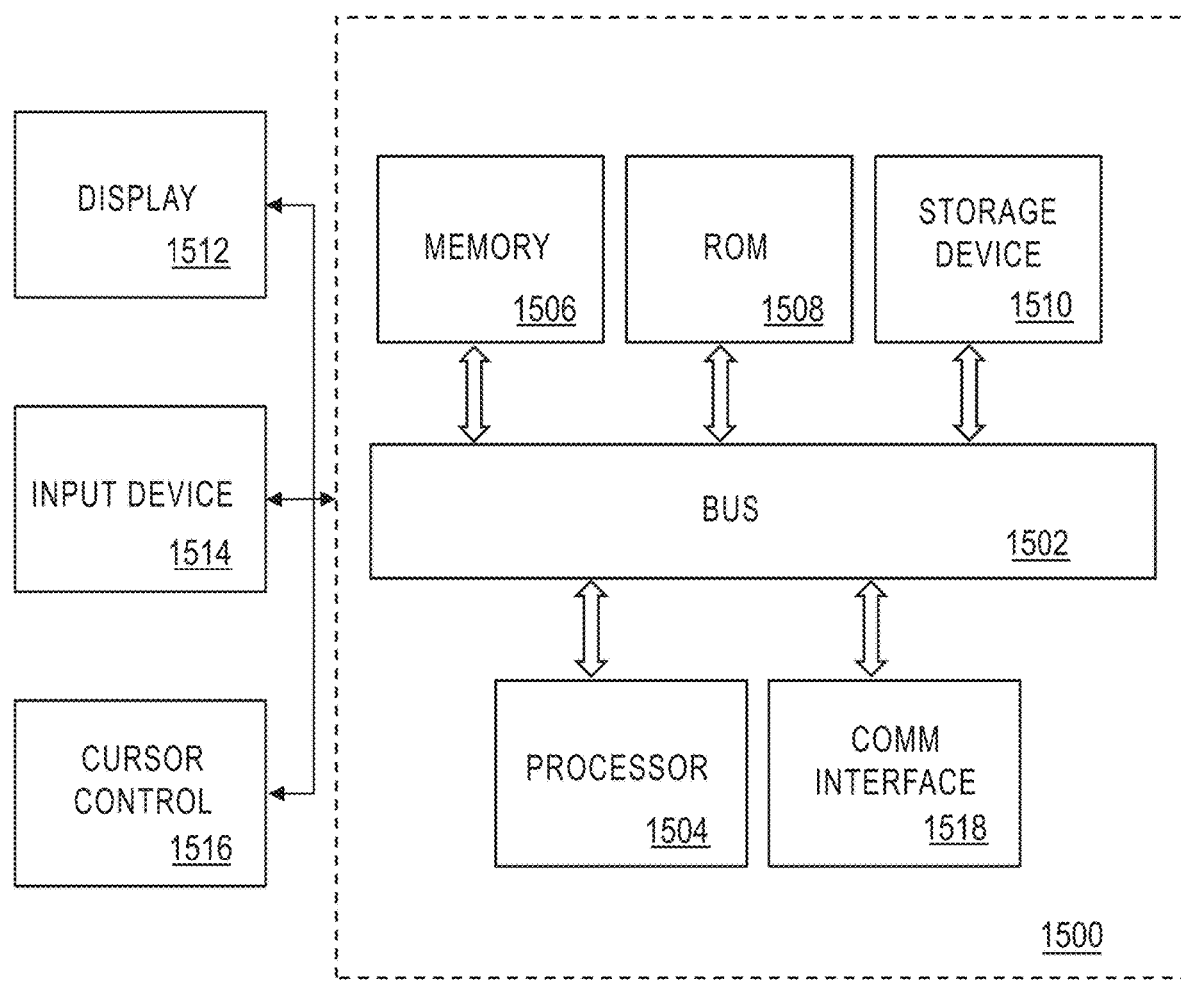
FIG. 15 illustrates an exemplary computing system for implementing various embodiments described herein.
Figure 16:
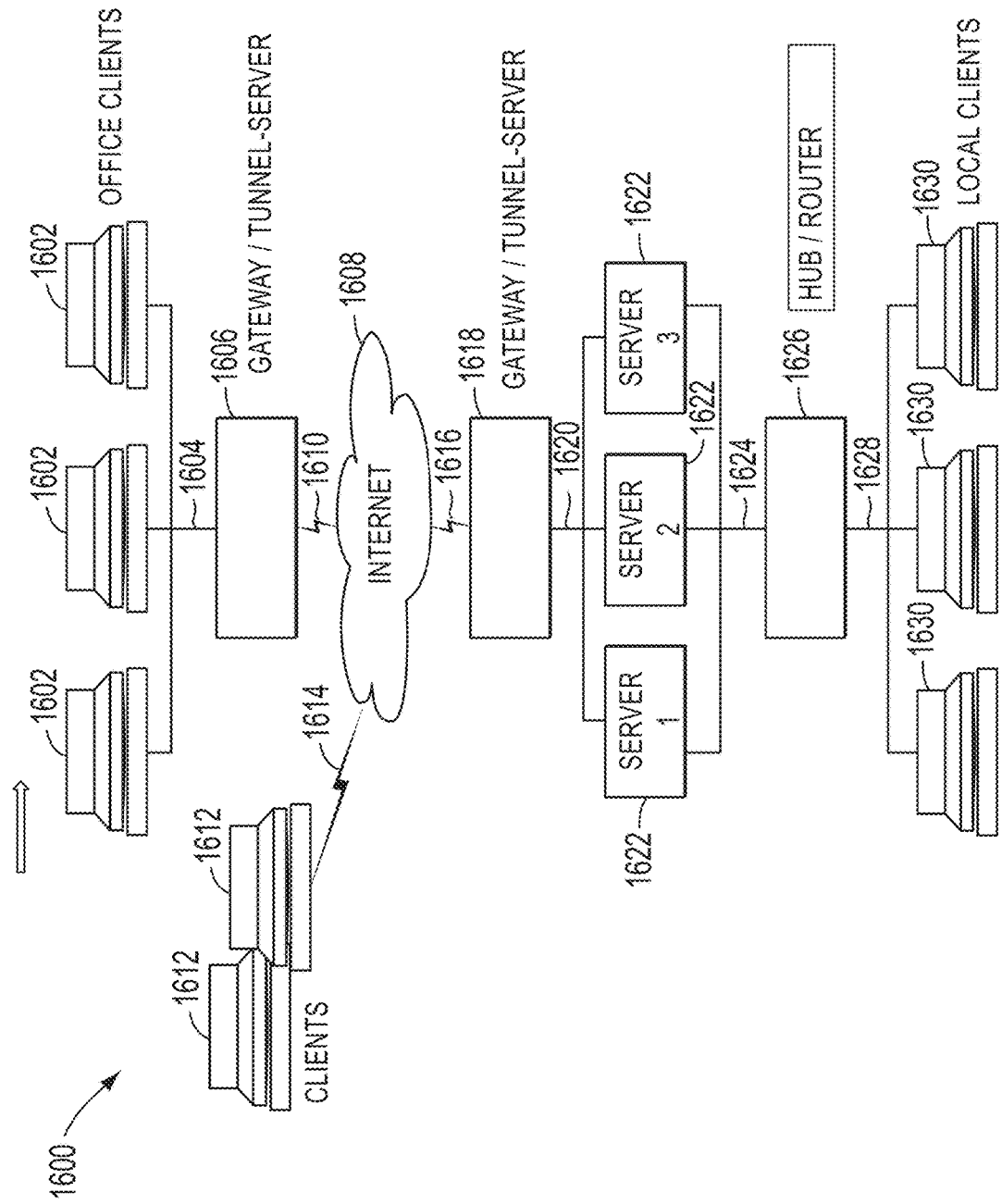
FIG. 16 illustrates an exemplary distributed network system according to various embodiments described herein.

FIG. 15 is a diagram illustrating an example system 1500 configured in accordance with one example embodiment. In system 1500, one or more servers 1522 can be configured to run the analysis applications for analyzing data sets produced by one or more devices or modalities 1540. The data included in the data sets can be stored in one or more storage devices 1550. Once the data sets have been uploaded to servers 1522, then a plurality of applications running on servers 1522 can be used to manipulate, analyze, and visualize the data sets from anywhere. For example, local client devices 1530 can be used to access servers 1522, e.g., through a hub or router 1526. At the same time, the data can be accessed remotely through remote client devices 1502, which are interfaced with servers 1522, e.g., via a gateway/hub/tunnel-server/etc. 1510, which is itself connected to the internet 1508 via some internet service provider (ISP) connection 1510, or remote client servers 1512, which are interfaced with servers 1522, e.g., via the internet 1508 and via an ISP connection 1514.

It should also be noted that devices 1540 can be directly interfaced with servers 1522, e.g., through the internet. In such embodiments, the collection application and functionality can reside on servers 1522, on devices 1540, or both. In other embodiments, devices 1540 can be interfaced with client devices 1502 or 1512. In such embodiments, the collection application or functionality can be included on client devices 1502 or 1512, devices 1540, or both.

Client devices 1502, 1512, and 1530 can be any kind of computing device that can be used to access servers 1522. As such, these devices can be laptop, desktop, or palmtop computers, terminals, mobile computing devices such as smartphones or tablets, etc. Servers 1522 can comprise one or more processors, servers, routers, co-processors, user interfaces, etc., whether co-located or located in different locations. In short, servers 1522 can comprise all of the resources, both hardware and software, needed to perform the functions described herein. A more detailed description of a computer system and the resources that can be used to implement the components illustrated in FIG. 15 is described below with respect to FIG. 3.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

FIG. 15 is a block diagram that illustrates a computer system 1500 that can be employed to carry out processing functionality, and to implement various components or subsystems of the systems described herein according to various embodiments. For example, system 1500 can comprise all or apportion of devices 1640, client devices, 1602, 1612, or 1630, servers 1622, etc. Computing system 1600 can include one or more processors, such as a processor 1604. Processor 1604 can be implemented using a general or special purpose processing engine such as, for example, a microprocessor, controller or other control logic. In this example, processor 1604 is connected to a bus 1602 or other communication medium.

Further, it should be appreciated that a computing system 1500 of FIG. 15 can be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 1500 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 1500 may be configured to connect to one or more servers in a distributed network. Computing system 1500 may receive information or updates from the distributed network. Computing system 1500 may also transmit information to be stored within the distributed network that may be accessed by other clients connected to the distributed network.

Computing system 1500 may include bus 1502 or other communication mechanism for communicating information, and processor 1504 coupled with bus 1502 for processing information.

Computing system 1500 also includes a memory 1506, which can be a random-access memory (RAM) or other dynamic memory, coupled to bus 1502 for storing instructions to be executed by processor 1504. Memory 1506 also may be used for storing temporary variables or other intermediate information during execution of instructions to be executed by processor 1504. Computing system 1500 further includes a read only memory (ROM) 1508 or other static storage device coupled to bus 1502 for storing static information and instructions for processor 1504.

Computing system 1500 may also include a storage device 1510, such as a magnetic disk, optical disk, or solid state drive (SSD) is provided and coupled to bus 1502 for storing information and instructions. Storage device 1510 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 1510 may include other similar instrumentalities for allowing computer programs or other instructions or data to be loaded into computing system 1500. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 1510 to computing system 1500.

Computing system 1500 can also include a communications interface 1518. Communications interface 1518 can be used to allow software and data to be transferred between computing system 1500 and external devices. Examples of communications interface 1518 can include a modem, a network interface (such as an Ethernet or other NIC card), a communications port (such as for example, a USB port, a RS-232C serial port), a PCMCIA slot and card, Bluetooth, etc. Software and data transferred via communications interface 1518 are in the form of signals which can be electronic, electromagnetic, and optical or other signals capable of being received by communications interface 1518. These signals may be transmitted and received by communications interface 1518 via a channel such as a wireless medium, wire or cable, fiber optics, or other communications medium. Some examples of a channel include a phone line, a cellular phone link, an RF link, a network interface, a local or wide area network, and other communications channels.

Computing system 1500 may be coupled via bus 1502 to a display 1512, such as a cathode ray tube (CRT) or liquid crystal display (LCD), for displaying information to a computer user. An input device 1514, including alphanumeric and other keys, is coupled to bus 1502 for communicating information and command selections to processor 1504, for example. An input device may also be a display, such as an LCD display, configured with touchscreen input capabilities. Another type of user input device is cursor control 1516, such as a mouse, a trackball or cursor direction keys for communicating direction information and command selections to processor 1504 and for controlling cursor movement on display 1512. This input device typically has two degrees of freedom in two axes, a first axis (e.g., x) and a second axis (e.g., y), that allows the device to specify positions in a plane. A computing system 1500 provides data processing and provides a level of confidence for such data. Consistent with certain implementations of embodiments of the present teachings, data processing and confidence values are provided by computing system 1500 in response to processor 1504 executing one or more sequences of one or more instructions contained in memory 1506. Such instructions may be read into memory 1506 from another computer-readable medium, such as storage device 1510. Execution of the sequences of instructions contained in memory 1506 causes processor 1504 to perform the process states described herein. Alternatively hard-wired circuitry may be used in place of or in combination with software instructions to implement embodiments of the present teachings. Thus, implementations of embodiments of the present teachings are not limited to any specific combination of hardware circuitry and software.

The term "computer-readable medium" and "computer program product" as used herein generally refers to any media that is involved in providing one or more sequences or one or more instructions to processor 1504 for execution. Such instructions, generally referred to as "computer program code" (which may be grouped in the form of computer programs or other groupings), when executed, enable the computing system 1500 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 1510. Volatile media includes dynamic memory, such as memory 1506. Transmission media includes coaxial cables, copper wire, and fiber optics, including the wires that comprise bus 1502.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1504 for execution. For example, the instructions may initially be carried on magnetic disk of a remote computer. The remote computer can load the instructions into its dynamic memory and send the instructions over a telephone line using a modem. A modem local to computing system 1500 can receive the data on the telephone line and use an infra-red transmitter to convert the data to an infra-red signal. An infra-red detector coupled to bus 1502 can receive the data carried in the infra-red signal and place the data on bus 1502. Bus 1502 carries the data to memory 1506, from which processor 1504 retrieves and executes the instructions. The instructions received by memory 1506 may optionally be stored on storage device 1510 either before or after execution by processor 1504.

It will be appreciated that, for clarity purposes, the above description has described embodiments with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Although various embodiments have been described with respect to certain exemplary embodiments, examples, and applications, it will be apparent to those skilled in the art that various modifications and changes may be made without departing from the present teachings.

What is claimed is:

1. A computer-implemented method of normalizing genotyping data, the method comprising:
   receiving a set of emission data from a plurality of substrates, wherein the emission data includes intensity of a first dye and intensity of a second dye, wherein the first dye indicates presence of a first target allele, and the second dye indicates presence of a second target allele;
   generating a plot of the set of emission data by plotting the intensity of the first dye versus the intensity of the second dye;
   normalizing the emission data in the plot based on an angular transformation, wherein the normalizing further includes:
      determining positions in the plot of high density of points;
      determining a set of data within a determined position with a minimum standard deviation as a reference; and
      determining an angle that produces a minimum theta standard deviation between the reference and remaining data to select the angular transformation; and
   wherein the method further comprises computing the 95th percentile signal of the reference to determine an amplitude scaling factor.

2. The computer-implemented method of claim 1, further comprising:
   normalizing the emission data in the plot based on amplitudes of the emission data.

3. A system for normalizing genotyping data, the system comprising: a memory; and
   a processor configured to:
   receive a set of emission data from a plurality of substrates, wherein the emission data includes intensity of a first dye and intensity of a second dye, wherein the first dye indicates presence of a first target allele, and the second dye indicates presence of a second target allele,
   generate a plot of the set of emission data by plotting the intensity of the first dye versus the intensity of the second dye,
   normalize the emission data in the plot based on an angular scaling transformation by:
      determining positions in the plot of high density of points;

determining a set of data within a determined position with a minimum standard deviation as a reference; and determining an angle that produces a minimum theta standard deviation between the reference and remaining data to select the angular transformation; and wherein the processor is further configured to compute the 95th percentile signal of the reference to determine an amplitude scaling factor.

4. The system of claim 3, wherein the processor is further configured to:

normalize the emission data in the plot based on amplitudes of the emission data.

* * * * *